US011332555B2

(12) United States Patent
Altenberg et al.

(10) Patent No.: US 11,332,555 B2
(45) Date of Patent: May 17, 2022

(54) POLYMER-ENCASED NANODISCS WITH IMPROVED BUFFER COMPATIBILITY

(71) Applicant: Texas Tech University System, Lubbock, TX (US)

(72) Inventors: Guillermo A. Altenberg, Lubbock, TX (US); Hongjun Liang, Lubbock, TX (US)

(73) Assignee: Texas Tech University System, Lubbock, TX (US)

( * ) Notice: Subject to any disclaimer, the term of this patent is extended or adjusted under 35 U.S.C. 154(b) by 78 days.

(21) Appl. No.: 17/064,687

(22) Filed: Oct. 7, 2020

(65) Prior Publication Data
US 2021/0171673 A1  Jun. 10, 2021

Related U.S. Application Data

(63) Continuation of application No. 16/117,073, filed on Aug. 30, 2018, now Pat. No. 10,829,571.

(60) Provisional application No. 62/552,605, filed on Aug. 31, 2017, provisional application No. 62/596,976, filed on Dec. 11, 2017.

(51) Int. Cl.
*C08F 8/40* (2006.01)
*C08L 89/00* (2006.01)
*C08L 33/00* (2006.01)
*C12N 9/14* (2006.01)
*C12N 11/04* (2006.01)
*C08F 8/12* (2006.01)
*C08F 2/38* (2006.01)
*C08F 8/44* (2006.01)
*C12N 9/96* (2006.01)
*C08F 222/08* (2006.01)
*C12N 11/082* (2020.01)

(52) U.S. Cl.
CPC ............ *C08F 8/40* (2013.01); *C08F 2/38* (2013.01); *C08F 8/12* (2013.01); *C08F 8/44* (2013.01); *C08F 222/08* (2013.01); *C08L 33/00* (2013.01); *C08L 89/00* (2013.01); *C12N 9/14* (2013.01); *C12N 9/96* (2013.01); *C12N 11/04* (2013.01); *C12N 11/082* (2020.01); *C12Y 306/01003* (2013.01); *C08F 2438/03* (2013.01)

(58) Field of Classification Search
CPC ...... C08F 8/40; C08F 8/12; C08F 8/44; C08F 2/38; C08F 2438/03; C08L 89/00; C08L 33/00; C12N 9/14; C12N 9/96; C12N 11/04; C12N 11/082; C12Y 306/01003
USPC .......................................................... 524/21
See application file for complete search history.

(56) References Cited

U.S. PATENT DOCUMENTS 9,937,152 B2 *  4/2018  Maeda ................ C08F 8/34
2016/0317672 A1 *  11/2016  Maeda ................ C08F 8/30

FOREIGN PATENT DOCUMENTS

WO  99009955 A1  3/1999
WO  2006/129127 A1  12/2006
WO  2008/065451 A2  6/2008

OTHER PUBLICATIONS

Fiori et al. "Polymer-encased nanodiscs with improved buffer compatibility", Scientific Reports, published online Aug. 7, 2017, vol. 7, Article No. 7432, pp. 1-10 (Year: 2017).*
Lindhoud et al. SMA-SH: Modified Styrene-Maleic Acid Copolymer for Functionalization of Lipid Nanodiscs', Biomacromolecules, 2016, vol. 17, pp. 1516-1522. (Year: 2016).*
Baruah, S.D. et al. "Styrene-maleic anhydride copolymers: Synthesis, characterization, and thermal properties." J Appl Polym Sci 60, 649-656 (1996).
BASF. Sokalan CP 9. Document TI/ES 1056 e. (2000).
Brewer, K.D., et al. "Reluctance to membrane binding enables accessibility of the synaptobrevin SNARE motif for SNARE complex formation." Proceedings of the National Academy of Sciences of the United States of America 108, 12723-12728 (2011).
Cooper, R.S. et al. "Association/dissociation of the nucleotide-binding domains of the ATP-binding cassette protein MsbA measured during continuous hydrolysis." The Journal of biological chemistry 288, 20785-20796 (2013).
Denisov, I.G. et al. "Nanodiscs for structural and functional studies of membrane proteins." Nature structural & molecular biology 23, 481-486 (2016).
Dominguez Pardo, J.J. et al. "Solubilization of lipids and lipid phases by the styrene-maleic acid copolymer." Eur Biophys J 46, 91-101 (2017).
Dorr, J.M. et al. "The styrene-maleic acid copolymer: a versatile tool in membrane research." Eur Biophys J 45, 3-21 (2016).
Etzkorn, M. et al. "Cell-free expressed bacteriorhodopsin in different soluble membrane mimetics: biophysical properties and NMR accessibility." Structure 21, 394-401 (2013).
Fiori, M. C. et al., "Polymer-encased nanodiscs with improved buffer compatibility", Scientific Reports, published online Aug. 7, 2017, vol. 7, Article No. 7432, pp. 1-10.
Fiori, M.C. et al. "Permeation of calcium through purified connexin 26 hemichannels." The Journal of biological chemistry 287, 40826-40834 (2012).
Friedrich, T. et al. "Proteorhodopsin is a light-driven proton pump with variable vectoriality." Journal of molecular biology 321, 821-838 (2002).

(Continued)

*Primary Examiner* — Michael M. Bernshteyn
(74) *Attorney, Agent, or Firm* — Edwin S. Flores; Daniel J. Chalker; Chalker Flores, LLP

(57) ABSTRACT

The present invention includes compositions, methods, and methods of making and using a polymer-encased nanodisc comprising: one or more integral membrane proteins in a lipid layer; and a polymer comprising zwitterionic styrene-maleic acid derivative repeating units that carry zero or nearly zero negative charge, and the polymer-encased nanodiscs.

10 Claims, 9 Drawing Sheets

(56) References Cited

OTHER PUBLICATIONS

Hagn, F., et al. "Optimized phospholipid bilayer nanodiscs facilitate high-resolution structure determination of membrane proteins." Journal of the American Chemical Society 135, 1919-1925 (2013).
International Search Report, PCT/US18/48840 (ISA/AU) dated Nov. 1, 2018.
Jamshad, M. et al. "Surfactant-free purification of membrane proteins with intact native membrane environment." Biochemical Society transactions 39, 813-818 (2011).
Knowles, T.J. et al. "Membrane proteins solubilized intact in lipid containing nanoparticles bounded by styrene maleic acid copolymer." Journal of the American Chemical Society 131, 7484-7485 (2009).
Kuang, L. et al. ""Frozen" block copolymer nanomembranes with light-driven proton pumping performance." ACS Nano 8, 537-545 (2014).
Lai, J.T., et al. "Functional polymers from novel carboxyl-terminated trithiocarbonates as highly efficient RAFT agents." Macromolecules 35, 6754-6756 (2002).
Leitz, A.J., et al. "Functional reconstitution of Beta2-adrenergic receptors utilizing self-assembling Nanodisc technology." Biotechniques 40, 601-602, 604, 606, passim (2006).
Li, G.Z. et al. "Investigation into thiol-(meth)acrylate Michael addition reactions using amine and phosphine catalysts." Polym Chem-Uk 1, 1196-1204 (2010).
Lindhoud, S. et al., 'SMA-SH: Modified Styrene-Maleic Acid Copolymer for Functionalization of Lipid Nanodiscs', Biomacromolecules, 2016, vol. 17, pp. 1516-1522.
Morrison, K.A. et al. "Membrane protein extraction and purification using styrene-maleic acid (SMA) copolymer: effect of variations in polymer structure." The Biochemical journal 473, 4349-4360 (2016).
Oluwole, A.O. et al. "Solubilization of Membrane Proteins into Functional Lipid-Bilayer Nanodiscs Using a Diisobutylene/Maleic Acid Copolymer." Angewandte Chemie 56, 1919-1924 (2017).
Patist, A., et al. "Importance of micellar kinetics in relation to technological processes." J Colloid Interface Sci 245, 1-15 (2002).
Rothnie, A.J. "Detergent-Free Membrane Protein Purification." Methods in molecular biology 1432, 261-267 (2016).
Rues, R.B., et al. "Co-translational formation and pharmacological characterization of beta1-adrenergic receptor/nanodisc complexes with different lipid environments." Biochimica et biophysica acta 1858, 1306-1316 (2016).
Scheidelaar, S. et al. "Effect of Polymer Composition and pH on Membrane Solubilization by Styrene-Maleic Acid Copolymers." Biophysical journal 111, 1974-1986 (2016).
Stahlberg, H. et al. "Two-dimensional crystals: a powerful approach to assess structure, function and dynamics of membrane proteins." FEBS letters 504, 166-172 (2001).
Urbatsch, I.L., et al. "P-glycoprotein is stably inhibited by vanadate-induced trapping of nucleotide at a single catalytic site." The Journal of biological chemistry 270, 19383-19390 (1995).
Viegas, A., et al. "The power, pitfalls and potential of the nanodisc system for NMR-based studies." Biol Chem (2016).
Wallin, E. et al. "Genome-wide analysis of integral membrane proteins from eubacterial, archaean, and eukaryotic organisms." Protein science: a publication of the Protein Society 7, 1029-1038 (1998).
Zoghbi, M.E., et al. "The Lipid Bilayer Modulates the Structure and Function of an ATP-binding Cassette Exporter." The Journal of biological chemistry 291, 4453-4461 (2016).

* cited by examiner

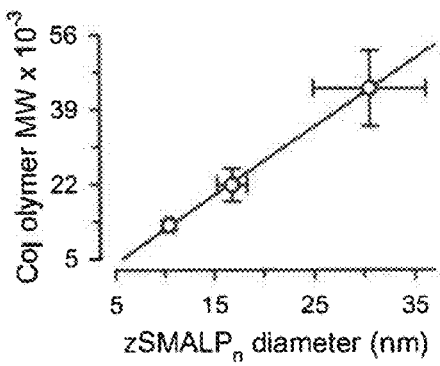

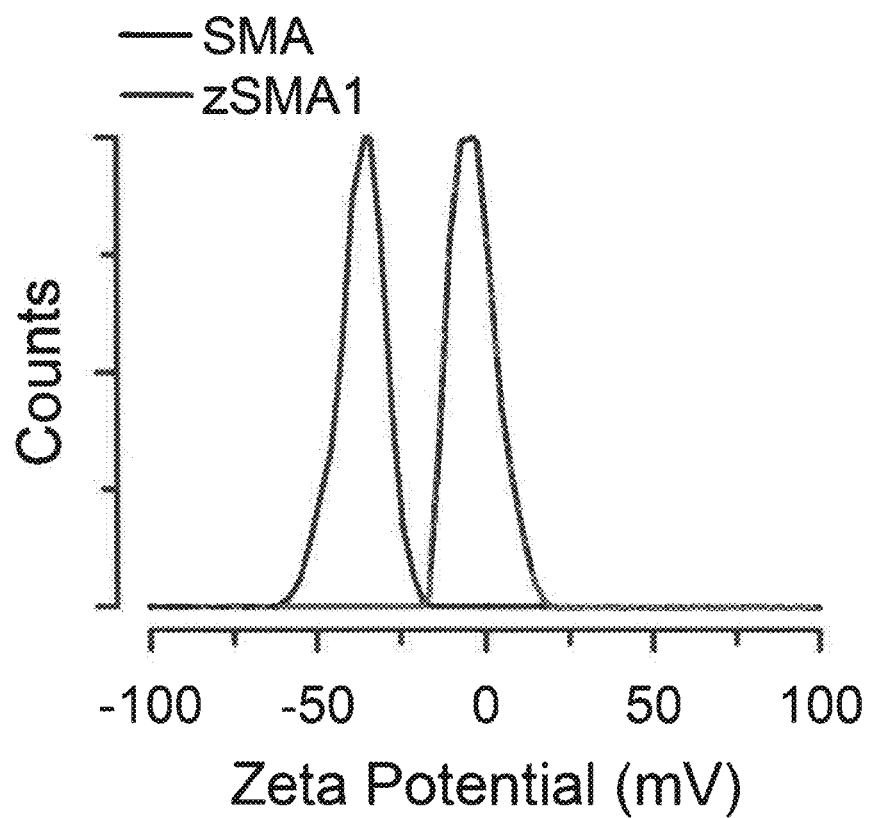
FIG. 6
Fig. 7A
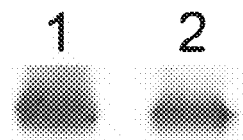
1: PR CM
2: PR-zSMALP1
Fig. 7B
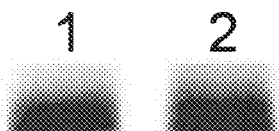
1: PR-LP
2: PR-zSMALP1

1: MsbA-DDM
2: MsbA-LP
3: MsbA-SMALPs
4: MsbA-zSMA1s

POLYMER-ENCASED NANODISCS WITH IMPROVED BUFFER COMPATIBILITY

CROSS-REFERENCE TO RELATED APPLICATIONS

This application is a continuation application of U.S. patent application Ser. No. 16/117,073 filed on Aug. 30, 2018 and which claims priority to U.S. Provisional Application Ser. No. 62/552,605, filed Aug. 31, 2017 and U.S. Provisional Application Ser. No. 62/596,976, filed Dec. 11, 2017, the entire contents of which are incorporated herein by reference.

STATEMENT OF FEDERALLY FUNDED RESEARCH

This invention was made with government support under DMR-1623241 and CBET-1623240 awarded by The National Science Foundation (NSF). The government has certain rights in the invention.

TECHNICAL FIELD OF THE INVENTION

The present invention relates in general to the field of lipid nanodiscs and transmembrane proteins.

BACKGROUND OF THE INVENTION

Without limiting the scope of the invention, its background is described in connection with lipid nanodiscs and transmembrane proteins.

Approximately 30% of genes in sequenced genomes correspond to membrane proteins, which are the targets of most drugs in medical use[1,2]. Accordingly, there is great interest in understanding the structure and function of this class of proteins. Integral membrane proteins, however, are harder to study than soluble proteins because they require a heterogeneous environment compatible with their hydrophobic and hydrophilic regions that normally interact with membrane lipids and the aqueous solutions on both sides of the membrane, respectively. For many studies, membrane proteins are extracted from cell membranes with detergents, purified when still solubilized in detergent, and then assayed in detergent or after reconstitution into a lipid bilayer membrane. The use of detergents is relatively simple, but they are far from ideal as membrane protein platforms. Differences in physicochemical properties such as curvature, lateral pressure profile and thickness, contribute to the reduced stability of proteins in detergent micelles compared to biomembranes[3-5]. Moreover, there are reports of significant structural and/or functional differences between membrane proteins studied in detergent micelles and in lipid bilayer membranes[6-11].

Reconstitution of membrane proteins into liposomes increases their stability, but significant drawbacks include the limited accessibility to the intraliposomal side and the liposomes' size, which complicates optical spectroscopy measurements due to light scattering. Nanodiscs (NDs) are a recent alternative that consists of two copies of a membrane scaffold protein that encase a small lipid bilayer patch[11]. Under optimal reconstitution conditions, NDs constitute a homogeneous and monodisperse population of proteolipid nanostructures that can be treated as soluble proteins. This is particularly advantageous for the implementation of methodologies such as fluorescence and solution NMR spectroscopies and single-particle electron cryo-microscopy[10,11]. A recent variant of the NDs are the polymer-encased NDs known as styrene-maleic acid (SMA)-lipid particles (SMALPs, also known as lipodisqs or native nanodiscs), where the membrane scaffold protein is replaced by amphipathic SMA copolymers[12-14]. There are two features of SMALPs that make them highly desirable. One is that SMA copolymers can be used to solubilize membranes directly, without detergent[12,14]. Another one is that SMALPs can be produced by mixing with membranes containing native lipids, allowing studies of membrane proteins in a closer to physiologic environment[12-14].

International Patent Application number PCT/GB1998/002546 (publication number WO1999009955 A2; equivalent to granted patents EP1 007002 and U.S. Pat. No. 6,426,905) discloses the use of hydrolyzed alternating copolymers of maleic anhydride (anionic, hydrophilic in its hydrolyzed maleic acid form) and either styrene or an alkyl vinyl ether (hydrophobic) to associate with phospholipids to form flattened disk-like molecular assemblies.

Also from the same inventor(s), International Patent Application number PCT/GB2006/050134 (publication number WO 2006/129127 A1) expands the composition to copolymer of styrene and maleic acid that is non-alternating, wherein the ratio of styrene to maleic acid repeating monomer units is greater than 1:1, and the copolymer and lipid associate to form macromolecular assemblies.

However, both patents teach that maleic acids are used in the copolymer composition, which have a $pK_a$ value in the region of 3.75-4.0 (Sugai, S and Ohno, N, Biophys. Chem. 1980 11: 387-395). The skilled artisan will recognize that at low pH (i.e., pH≤4), a significant portion of the maleic acid repeating units will exist in a protonated form that is fairly hydrophobic, hence instead of interacting with lipid to form soluble nanodiscs, the copolymer would precipitate out from aqueous solutions. By contrast, at high pH (i.e. pH≥5) a significant portion of the maleic acid repeating units will exist in a de-protonated form that is amenable to complexation with cationic polyvalent ions, which again leads to the precipitation of the copolymer out from aqueous solutions. This incompatibility with pH variations and presence of polyvalent cations is a significant limitation of traditional SMALP technology. This incompatibility was only partially addressed in the International Patent Application number PCT/GB2006/050134 (publication number WO 2006/129127 A1), in which non-alternating styrene and maleic acid copolymer is used and it teaches that depending on the stoichiometric ratio between styrene and maleic acid units, the applicable pH range to form the well-dispersed copolymer-lipid macromolecular assemblies can be expanded slightly to pH 5.0-7.5. The incompatibility of the copolymer with the presence of polyvalent cations was not addressed in this patent.

In a follow-up patent from the same inventor(s), International Patent Application number PCT/GB2007/050730 (publication number WO 2008/065451 A2), the pH incompatibility issue of the lipidic macromolecular assemblies was addressed by replacing the styrene and maleic acid copolymer entirely with surfactants that do not carry carboxylic acid functions. However, those surfactant-lipid macromolecular assemblies represent a different family of lipidic membrane platforms (e.g., bicelles as reported in Howard K P and Opella S J, J. Magn. Reson. B., 1996 112: 91-94).

In summary, despite the disclosure of SMA-lipid macromolecular assemblies as early as in 1997 (International Patent Application number PCT/GB1998/002546, publication number WO1999009955 A2), and a series of follow-up disclosures as well as academic publications since then, traditional SMALP technology is consistently limited by the range of pH and the presence of polyvalent cations it is incompatible with (see for example, a recent review paper by Dorr J M et al, Eur Biophys J 2016 45:3-21). Tuning the stoichiometric ratio between styrene and maleic acid units (International Patent Application number PCT/GB2006/050134; publication number WO 2006/129127 A1) only expands slightly the applicable pH range to pH 5.0-7.5 without addressing the incompatibility issue with polyvalent cations, and replacing SMA copolymers with surfactant (International Patent Application number PCT/GB2007/050730; publication number WO 2008/065451 A2) helps solve the pH incompatibility issue but results in a different family of lipidic membrane platforms.

In spite of the current excitement about SMALPs, their use is strictly limited by the incompatibility of SMA and SMALPs with low pH solutions and some cationic solutes. Therefore, a need remains for improved nanodiscs that operate at some physiological conditions such as low-pH environment, and the need of these proteins to interact with polyvalent cations under physiological conditions.

SUMMARY OF THE INVENTION

In one embodiment, the present invention includes polymer-encased nanodiscs with improved buffer compatibility comprising: a polymer comprising styrene-maleic acid derivative repeating units that carry zero or nearly zero net negative charge:

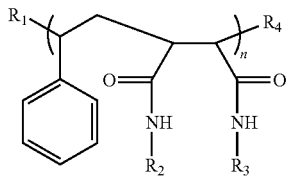

wherein the distribution of styrene and maleic acid derivative repeating units is random, and the resultant nanodiscs are compatible with at least one of polyvalent cations, $MgCl_2$, $CaCl_2$, or pH<5.

In another embodiment, the present invention includes polymer-encased nanodiscs with improved buffer compatibility comprising: a polymer comprising zwitterionic styrene-maleic acid (zSMA) repeating units:

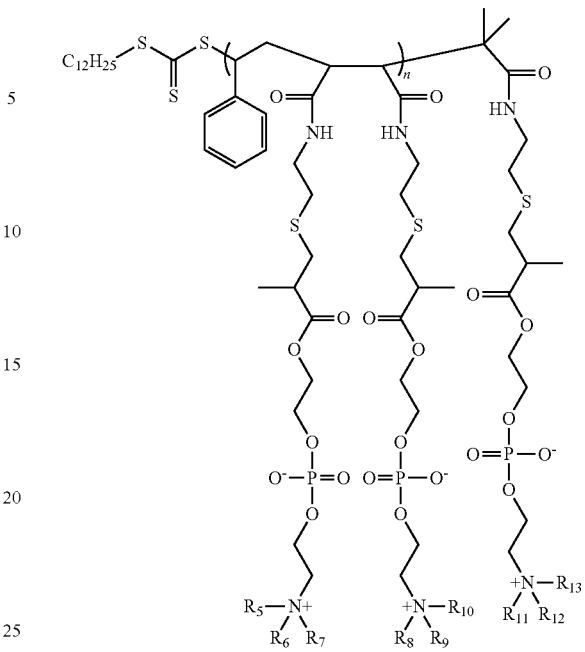

wherein the distribution of styrene and maleic acid derivative repeating units is random, and the zSMA is compatible with at least one of polyvalent cations, $MgCl_2$, $CaCl_2$, or pH<5.

In one aspect, $R_1$, $R_2$, $R_3$, $R_4$ carry zero or nearly zero net negative charge and are selected from hydrogen; deuterium; a halogen group; a nitrile group; a nitro group; an imide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group including one or more of N, O, or S atoms; and wherein n is 1 to 200. In another aspect, n is 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 185, 190, 195, 200, or more. In another aspect, $R_1$, $R_2$, $R_3$, $R_4$ are all hydrophilic. In another aspect, some of the $R_1$, $R_2$, $R_3$, $R_4$ are hydrophilic (such as $R_2$, $R_3$) while others are not (such as $R_1$, $R_4$).

In another aspect, $R_2$ and/or $R_3$ are not bonded with the polymer repeating units via amide bond(s), rather via ester bond(s), ether bond(s), thioester bond(s), alkyl bond(s) or other forms of chemical bonding;

Yet in another aspect, $R_1$ and/or $R_4$ are not bonded with the polymer backbone via C—C bonds, rather via other forms of chemical bonding including but are not limited to amide, ester, ether, silyl, urea, etc.

In another aspect, $R_1$, $R_2$, $R_3$, $R_4$ carry zwitterionic functional groups, such as $-PO_4^- -(CH_2)_k - N^+(R)_3$, $-N^+$ (R)$_2$—(CH$_2$)$_k$—PO$_4^-$, —N$^+$(R)$_2$—(CH$_2$)$_k$—SO$_3^-$, or other constructions of similar structure, in which k is 1, 2, 3, 4 or more, and R represents a substituted or unsubstituted alkyl group, a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group including one or more of N, O, or S atoms.

In another aspect, some of the $R_1$, $R_2$, $R_3$, $R_4$ carry zwitterionic functional groups (such as $R_2$, $R_3$) while others do not (such as $R_1$, $R_4$).

In another aspect, the polymer is composed of zwitterionic styrene-maleic acid derivative (zSMA) repeating units:

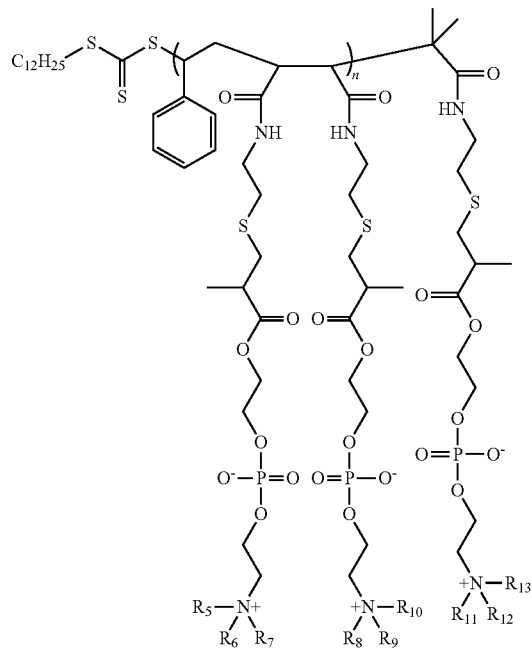

wherein the distribution of styrene and maleic acid derivative repeating units is random, and the nanodiscs are compatible with at least one of polyvalent cations, MgCl$_2$, CaCl$_2$, or pH<5.

In one aspect, $R_5$, $R_6$, $R_7$, $R_8$, $R_9$, $R_{10}$, $R_{11}$, $R_{12}$, $R_{13}$ are selected from hydrogen; deuterium; a halogen group; a nitrile group; a nitro group; an imide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group including one or more of N, O, or S atoms; and wherein n is 1 to 200. In another aspect, n is 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 185, 190, 195, 200, or more.

In another aspect, one or more end groups of zSMA (e.g. C$_{12}$H$_{25}$—S—(C=S)—S—) are introduced by reversible addition-fragmentation chain-transfer (RAFT) polymerization in the preparation of zSMA using S-1-dodecyl-S'-(α, α'-dimethyl-α"-acetic acid)trithiocarbonate (DATC) as the chain transfer agent. In another aspect, one or more end groups of zSMA introduced by RAFT chain transfer agents that are cleaved or converted to other chemical groups, including but not limited to thiol, hydroxyl, carboxyl, amine, and alkyl groups. In another aspect, the zSMA is prepared via other polymerization methods selected from at least one of anionic polymerization, cationic polymerization, conventional free radical polymerization, or other types of controlled/living free radical polymerization such as atom transfer radical polymerization (ATRP), and nitroxide mediated polymerization (NMP).

In another embodiment, the present invention includes a method of making a nanodisc with improved buffer compatibility comprising: mixing the one or more integral membrane proteins in a lipid layer with a polymer comprising styrene-maleic acid derivative repeating units, wherein the nanodiscs are compatible with at least one of polyvalent cations, MgCl$_2$, CaCl$_2$, or pH<5. In one aspect, one or more of $R_1$, $R_2$, $R_3$, $R_4$, $R_5$, $R_6$, $R_7$, $R_8$, $R_9$, $R_{10}$, $R_{11}$, $R_{12}$, $R_{13}$ are selected from hydrogen; deuterium; a halogen group; a nitrile group; a nitro group; an imide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group including one or more of N, O, or S atoms; and wherein n is 1 to 200. In another aspect, n is 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 185, 190, 195, 200, or more.

In another aspect, the present invention includes a method of making a nanodisc with improved buffer compatibility comprising: mixing the native cell membranes carrying integral membrane proteins with a polymer comprising styrene-maleic acid derivative repeating units, wherein the solubilized nanodiscs are compatible with at least one of polyvalent cations, $MgCl_2$, $CaCl_2$, or pH<5. In one aspect, one or more of $R_1$, $R_2$, $R_3$, $R_4$, $R_5$, $R_6$, $R_7$, $R_8$, $R_9$, $R_{10}$, $R_{11}$, $R_{12}$, $R_{13}$ are selected from hydrogen; deuterium; a halogen group; a nitrile group; a nitro group; an imide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group including one or more of N, O, or S atoms; and wherein n is 1 to 200. In another aspect, n is 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 185, 190, 195, 200, or more.

In another aspect, the one or more end groups of zSMA (e.g. $C_{12}H_{25}$—S—(C=S)—S—) are introduced by reversible addition-fragmentation chain-transfer (RAFT) polymerization in the preparation of zSMA using S-1-dodecyl-S'-($\alpha,\alpha'$-dimethyl-$\alpha''$-acetic acid)trithiocarbonate (DATC) as the chain transfer agent. In another aspect, the one or more end groups of zSMA introduced by RAFT chain transfer agents that are cleaved or converted to other chemical groups, including but not limited to thiol, hydroxyl, carboxyl, amine, and alkyl groups. In another aspect, the zSMA is prepared via other polymerization methods selected from at least one of anionic polymerization, cationic polymerization, conventional free radical polymerization, or other types of controlled/living free radical polymerization such as atom transfer radical polymerization (ATRP), and nitroxide mediated polymerization (NMP). In another aspect, the one or more integral membrane proteins are soluble at a pH<7.0. In another aspect, the one or more integral membrane proteins are soluble in the presence of cations. In another aspect, the one or more integral membrane proteins are adapted for the determination of acidification-induced rhodopsins spectral shifts, activation of ion channels (such as KcsA), or measurement of ATPases. In another aspect, the one or more integral membrane proteins are rhodopsins, ion pumps, ATP-binding cassette proteins. In another aspect, the one or more integral membrane proteins are at least one of P-type, F-type, V-type, or ABC ATPases. In another aspect, the lipids comprise lipids isolated from cells. In another aspect, the lipids comprise synthetic lipids. In another aspect, the zwitterionic styrene-maleic acid polymer has the structure:

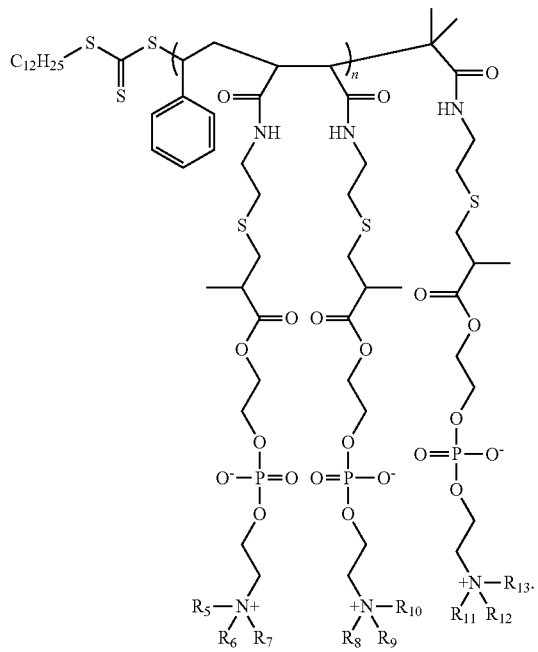

A composition comprising:

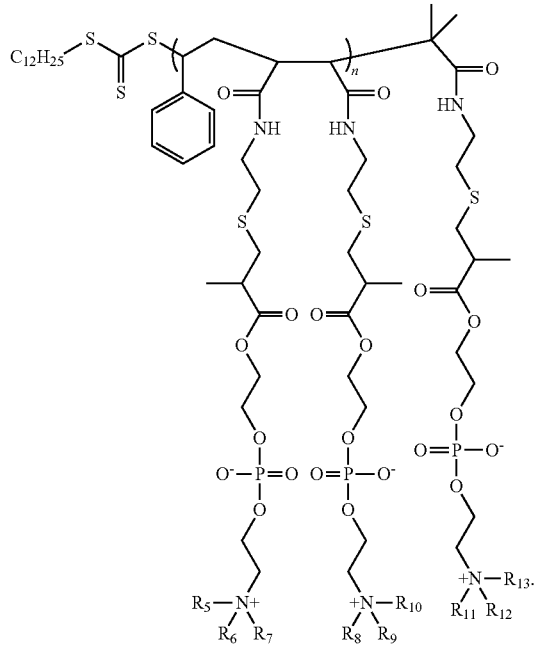

In one aspect, $R_5$, $R_6$, $R_7$, $R_8$, $R_9$, $R_{10}$, $R_{11}$, $R_{12}$, $R_{13}$ are selected from hydrogen; deuterium; a halogen group; a nitrile group; a nitro group; an imide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group including one or more of N, O, or S atoms; and wherein n is 1 to 200. In another aspect, n is 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 185, 190, 195, 200, or more.

In another embodiment, the present invention includes a composition made by a method comprising:

1

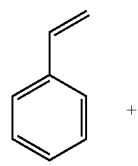

+

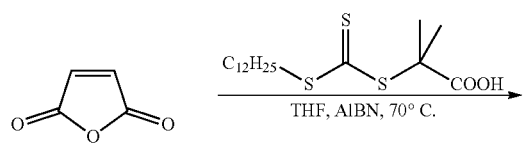

↓

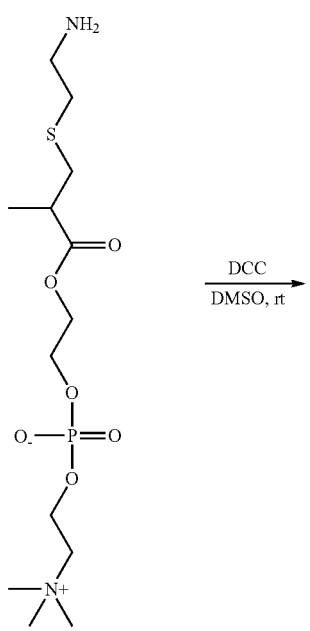

2

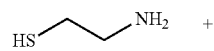 +

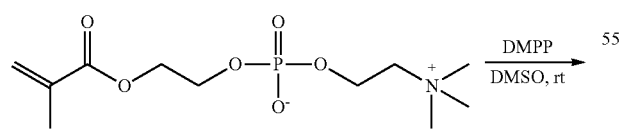

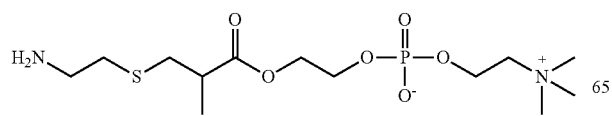

-continued

3

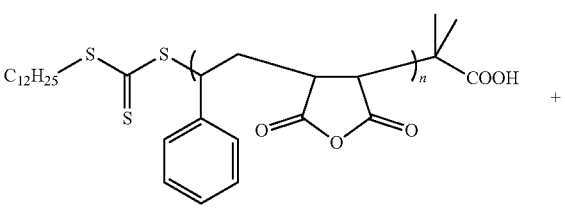

+

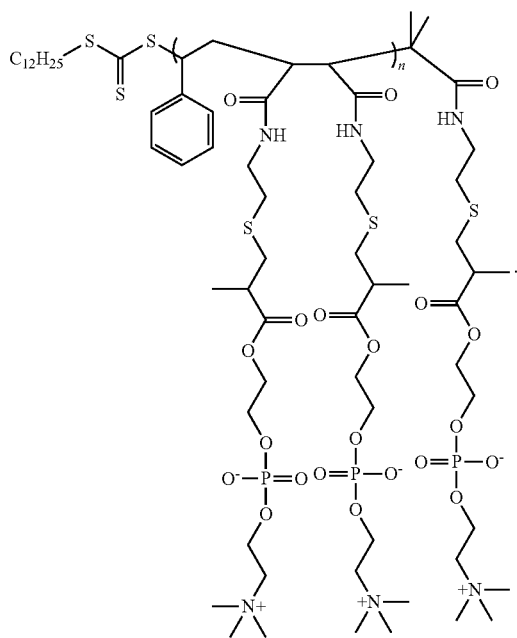

In one aspect, $R_5$, $R_6$, $R_7$, $R_8$, $R_9$, $R_{10}$, $R_{11}$, $R_{12}$, $R_{13}$, in accordance to the following structure:

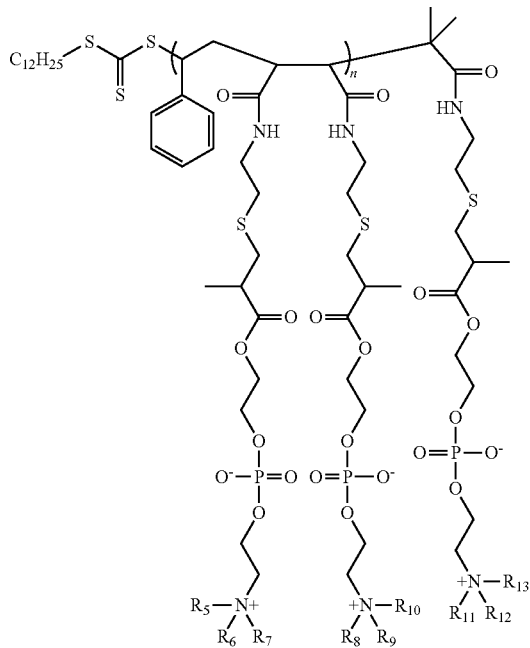

are selected from hydrogen; deuterium; a halogen group; a nitrile group; a nitro group; an imide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group including one or more of N, O, or S atoms; and wherein n is 1 to 200. In another aspect, n is 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 185, 190, 195, 200, or more. In another aspect, the one or more end groups of zSMA (e.g. $C_{12}H_{25}$—S—(C=S)—S—) are introduced by reversible addition-fragmentation chain-transfer (RAFT) polymerization in the preparation of zSMA using S-1-dodecyl-S'-(α,α'-dimethyl-α"-acetic acid)trithiocarbonate (DATC) as the chain transfer agent. In another aspect, the one or more end groups of zSMA introduced by RAFT chain transfer agents that are cleaved or converted to other chemical groups, including but not limited to thiol, hydroxyl, carboxyl, amine, and alkyl groups. In another aspect, the zSMA is prepared via other polymerization methods selected from at least one of anionic polymerization, cationic polymerization, conventional free radical polymerization, or other types of controlled/living free radical polymerization such as atom transfer radical polymerization (ATRP), and nitroxide mediated polymerization (NMP).

BRIEF DESCRIPTION OF THE DRAWINGS

For a more complete understanding of the features and advantages of the present invention, reference is now made to the detailed description of the invention along with the accompanying figures and in which:

(FIG. 1A) SMA nanodiscs (SMALPs). Crude membranes from *E. coli* expressing recombinant PR (tube 1) were solubilized with SMA (Xiran, see text; tube 2). The solubilized material obtained after centrifugation (tube 3) was visualized in the absence of buffer changes (tube 3) or after addition of $MgCl_2$ (tube 4), $CaCl_2$ (tube 5) or HCl (tube 6). The final concentrations of $MgCl_2$ and $CaCl_2$ were 5 mM. The pH in all tubes was 8, except for tube 6 were pH was 5. (FIG. 1B) zSMA1 nanodiscs (zSMALP1s). See legend of panel A for details. See Methods for additional details. (FIG. 1C) Structure of an exemplary zSMA copolymer. The letter n signifies the number of repeats. (FIG. 1D) Size-exclusion chromatography. Liposomes formed by *E. coli* total lipids were solubilized by SMA, zSMA1, zSMA2 or zSMA3, and the solubilized material was run on a Superdex 200 Increase size-exclusion column (see Methods for details). $A_{280}$: absorbance at 280 nm. (FIG. 1E) Hydrodynamic diameter. The graph shows typical examples of different preparations illustrating their size distribution. (FIG. 1F) Summary of hydrodynamic diameter data (left graph). Means±SEM of experiments such as those presented in FIG. 1E for nanodiscs formed by SMA (n=4), zSMA1 (n=6), zSMA2 (n=5) and zSMA3 (n=6). Relationship between the molecular weight of the P(S-at-MA) alternating copolymers (determined by NMR and the zSMALPs diameter (determined by DLS) (right graph). Values are presented as means±polydispersity. The line corresponds to a linear fit.

(FIG. 2A) pH-induced PR spectral shift elicited by lowering from 8 to 5. The data were normalized to the peak absorbance. The inset shows that the emission maximum is not clearly identifiable at pH 5 with the PR in SMALPs. At pH 5 the $A_{520}$ of PR in SMALPs nm decreased to 39% of the value at pH 8 (n=2), due to precipitation (see FIG. 1A, tube 6). In contrast, the $A_{520}$ of PR in zSMAP1s at pH 5 did not decrease (138±13%; n=3). (FIG. 2B) ATPase activity of MsbA. The ATPase activity of MsbA in zSMALP1s was slightly higher than that MsbA in the detergent DDM (P<0.005; n=6 for each condition). The data were normalized to the average activity in DDM (0.34±0.03 ATP/s; n=6). The activity of MsbA in SMALPs could not be measured because of the precipitation of MsbA-SMALPs in the presence of $MgCl_2$.

(FIG. 4A) NMR spectrum of DATC. (FIG. 4B) NMR spectrum P(S-at-MA)$_{59}$. (FIG. 4C) NMR spectrum of P(S-at-MA)$_{106}$. (FIG. 4D) NMR spectrum of P(S-at-MA)$_{215}$. DATC was dissolved in $CHCl_3$ and the alternating copolymers were dissolved in acetone-$d_6$.

(FIG. 5A) NMR spectrum of cysteamine-PC. (FIG. 5B) NMR spectrum of cysteamine- PC-modified P(S-at-MA)$_{59}$. (FIG. 5C) NMR spectrum of cysteamine-PC-modified P(S-at-MA)$_{106}$. (FIG. 5D) NMR spectrum of cysteamine-PC-modified P(S-at-MA)$_{215}$. Compounds were dissolved in D$_2$O.

FIG. 6 shows the zeta potential. (FIG. 6) The zeta potentials of commercial SMA (black) and P(S-at-MA)$_{215}$ (red) are shown.

FIGS. 7A and 7B show the solubilization by zSMA1 of proteorhodopsin (PR) from membranes. (FIG. 7A) Solubilization of PR from crude membranes. Lane 1 (PR CM): PR in the crude membranes; lane 2 (PR-zSMALP1): PR solubilized into zSMALP1s. Equivalent volumes were loaded. (FIG. 7B) Solubilization of purified PR reconstituted into liposomes. Lane 1 (PR-PL): PR reconstituted into liposomes; lane 2 (PR-zSMALP1): PR solubilized into zSMALP1s. The equivalent volume run in lane 2 was twice that run on lane 1. The data correspond to immunoblots using a primary antibody against the His tag fused to the C-terminal end of PR.

DETAILED DESCRIPTION OF THE INVENTION

Figure 1A:
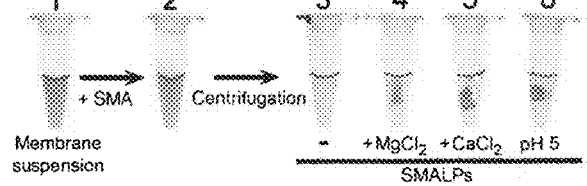
FIGS. 1A to 1F show the characterization of nanodiscs formed by zSMAs.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

The disclosed invention includes a method to prepare a polymer designed to replace the membrane scaffold proteins (MSPs) in nanodiscs. The disclosed invention also encompasses a polymer nanodisc comprising the synthetic MSP, as well as synthetic lipid replacements, to arrive at a completely synthetic nanodisc.

The polymer comprising styrene-maleic acid derivative repeating units of the present invention overcomes the many problems in the prior art because the styrene-maleic acid derivative repeating units disclosed herein carry zero or nearly zero net negative charge and can be prepared and used to encase lipidic nanodiscs with improved buffer compatibility with both pH variations and the presence of polyvalent cations.

In one aspect, the present invention copolymer has a structure

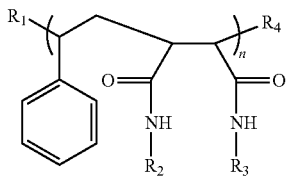

in which the maleic acid derivative unit is converted from a maleic anhydride unit into a styrene-maleic anhydride copolymer. It should be pointed out that the abovementioned general chemical representation of the disclosed polymer does not suggest that the styrene repeating unit and maleic acid derivative repeating unit must arrange themselves in an alternating manner. To those skilled in the art of polymer chemistry, the copolymerization of styrene and maleic anhydride is an extremely well characterized polymerization reaction. The reactivity ratios, $r_1$ and $r_2$, for any monomer pair may be used as an index for evaluating the alternating frequency in copolymerization reactions. Ideal random copolymerization occurs when $r_1$, $r_2$ and $r_1 r_2$ are equal to 1. When $r_1$, $r_2$ and $r_1 r_2$ tend to zero, the degree of alternating copolymerization increases. The reactivity ratios $r_1$ and $r_2$ of styrene (monomer 1) with maleic anhydride (monomer 2) are 0.097 and 0.001, respectively (Fried, J. R., Polymer Science and Technology, 3rd Ed, Prentice Hall (2014), ISBN 0137039557), indicating that although both monomers preferentially react with each other, styrene is significantly less discriminating than maleic anhydride. Consequently, the sequence distribution within a copolymer of styrene and maleic anhydride will depend on the monomer feeding ratio and the resulting copolymers can differ from 1:1 alternation. In cases where the ratio of styrene to maleic anhydride is greater than 1:1 (for example 2:1, 3:1 or 4:1) an increasing number of styrene-styrene sequences are present.

The styrene-maleic acid derivative copolymer of the present invention can be preferentially prepared by controlled/"living" polymerization methods as specified hereinbelow. Without wishing to be bound by a theory, the inventors hypothesize that a well-defined copolymer prepared by controlled/"living" polymerization methods offers one or more of the following advantages over commercially available styrene-maleic anhydride copolymer that is often prepared by conventional polymerization methods and has poorly controlled molecular weight distribution (i.e., polydispersity index or PDI; PDI is defined as the ratio of $M_w$ to $M_n$, where $M_w$ is the weight-averaged molecular weight and $M_n$ is the number-averaged molecular weight (Sperling L H, Introduction to Polymer Science, 4th edition, Wiley 2006. ISBN: 047170606)): (1) Well-controlled styrene-maleic acid derivative copolymers support the formation of nanodiscs with well-controlled diameters at high yields; (2) Tuning nanodisc diameters is possible by tuning precisely the chain sizes of styrene-maleic acid derivative copolymers; and/or (3) The well-controlled end functions of styrene-maleic acid derivative copolymers resulting from the controlled/"living" polymerization methods offer facile modification strategies to conjugate with various desired molecules, which are of interest for a variety of applications, such as biomolecules, antibody, protein or peptides, affinity tags, targeting devices, small molecules, fluorescent labels, therapeutic agents, micro- and nanoparticles, pharmaceutically active moieties, macromolecules, diagnostic labels, chelating agents, dispersants, charge modifying agents, viscosity modifying agents, surfactants, coagulation agents and flocculants, as well as various combinations of these chemical compounds. In certain embodiments, two or more different chemical compounds can be used to produce multifunctional derivatives. These conjugation chemistries are well known in the art (for example, Michael B S, March's Advanced Organic Chemistry: Reactions, Mechanisms, and Structure Advanced Organic Chemistry, 7$^{th}$ edition, Wiley 2013, ISBN: 0470462590), relevant portions incorporated herein by reference.

The disclosed styrene-maleic acid derivative copolymer can be also prepared by conventional polymerization methods as well known in the art (Painter P C and Coleman M M, Essentials of Polymer Science and Engineering, DEStech Publication, Inc., 2009. ISBN: 9781932978756), relevant portions incorporated herein by reference, or prepared from commercially available raw materials (i.e. styrene-maleic anhydride copolymers) to reduce the cost. Commercially available styrene-maleic anhydride copolymers may be obtained from, e.g., Malvern Cosmeceutics (Worcester, UK), Sigma-Aldrich (St. Louis, Mo., USA), TOTAL Cray Valley (Beaufort, Tex., USA), and Polyscope (Geleen, NL), among others.

An example of the disclosed zwitterionic styrene-maleic acid derivative copolymer of the present invention has the structure:

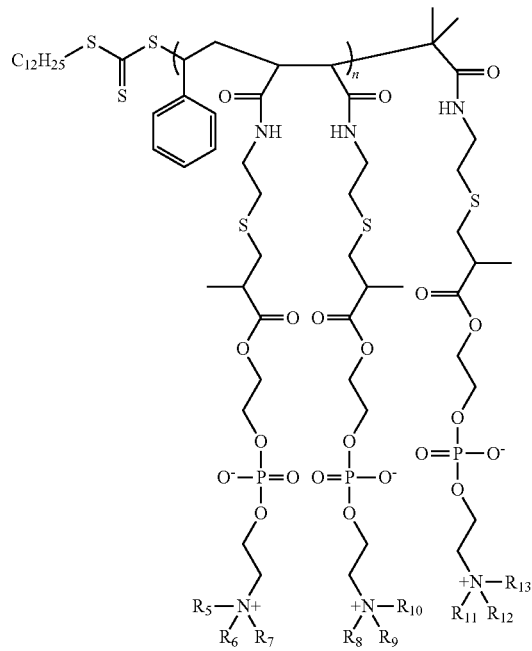

It should be pointed out that the . . . C—S—C . . . linkage chemistry between zwitterionic function groups and the maleic acid derivative repeating unit represents only one of the many possibilities for synthesis. As will be understood by those of skill in the art, the . . . C—S—C . . . linkage can be replaced by numerous other functional groups. Such functional groups include, but are not limited to, nucleophilic and electrophilic groups, and acidic and basic groups, e.g., carbonyl groups, amino groups, nitrate groups, sulfate groups, ether groups, and hydrocarbyl groups such as alkyl, aryl, vinyl and allyl groups, or a combination of such. These linkage chemistry is well known in the art (for example, Michael B S, March's Advanced Organic Chemistry: Reactions, Mechanisms, and Structure Advanced Organic Chemistry, 7$^{th}$ edition, Wiley 2013, ISBN: 0470462590), relevant portions incorporated herein by reference.

Due to the structural difference of the copolymers, the disclosed polymer-encased nanodiscs offer the following unique advantages in comparison to traditional SMA-lipid macromolecular complexes: For example: (1) there is no limitation on pH (in particular, the disclosed polymer-encased nanodiscs are stable in a wide range of pH conditions including pH<5, which is frequently encountered in digestive tract (e.g., gut), lysosomes, cancer sites, and inflammatory sites etc.); (2) there is no limitation on the presence of polyvalent ions such as $Mg^{2+}$, $Ca^{2+}$, etc., which are indispensable component in all intracellular and extracellular fluids; (3) the diameters of nanodiscs can be tuned conveniently by the sizes of the styrene-maleic acid derivative copolymer chains; and/or (4) various diagnostic and therapeutic agents can be easily conjugated at the ends of the styrene-maleic acid derivative copolymer chains for fundamental studies of the nanodiscs, or using the nanodiscs as platforms for biomedical and biotechnological applications.

As a result of those important differences, polymer-encased nanodiscs disclosed herein can: (1) fulfill the applications expected for conventional SMA-lipid macromolecular complexes, such as therapy (e.g., for ophthalmic use such as in the treatment of the condition known as "dry eye" syndrome; (2) can be used for lubricating biological membranes (e.g. synovial); (3) can be used for treatment of the surfaces of articulated joints in connection with arthritic conditions or to lubricate surfaces of medical devices and prostheses, e.g., delivering active agents locally to the lung or, via the highly permeable membranes lining the deep lung, into the systemic circulation, to name a few). Furthermore, the polymer-encased nanodiscs disclosed herein open up new opportunities beyond the reach of conventional SMA-lipid macromolecular complexes, such as drug delivery that will need to survive lysosome trapping, drug delivery for cancer therapy or inflammatory treatment, drug delivery through digestive tract, and the structural and functional characterization of membrane proteins or peptides that requires the presence of polyvalent cations or low pH, to name a few. These structural and functional characterization methods include various spectroscopy approaches such as nuclear magnetic resonance (NMR), circular dichroism (CD), Fourier-transform infrared (FTIR) spectroscopies, to name a few, as well as x-ray diffraction (XRD) crystallography, cryo-electron microcopy (cryo-EM), etc., where maintaining the stability of membrane proteins or peptides carried by the disclosed polymer-encased nanodiscs under physiologically relevant buffer conditions (i.e., low pH or the presence of polyvalent cations) is a prerequisite.

The present invention includes the zwitterionic styrene-maleic acid polymer having a structure:

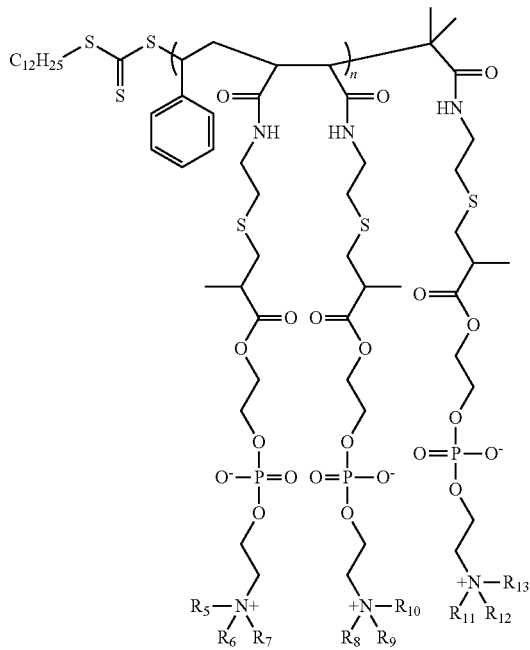

wherein $R_5$, $R_6$, $R_7$, $R_8$, $R_9$, $R_{10}$, $R_{11}$, $R_{12}$, $R_{13}$ are selected from hydrogen; a halogen group; a nitrile group; a nitro group; an imide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group including one or more of N, O, or S atoms and wherein n is 1 to 200.

The end groups of zSMA (e.g. $C_{12}H_{25}$—S—(C=S)—S—) shown in this structure are merely one example of the possible end groups of the zSMA, in this case they were introduced by reversible addition-fragmentation chain-transfer (RAFT) polymerization in the preparation of zSMA using S-1-dodecyl-S'-($\alpha,\alpha'$-dimethyl-$\alpha''$-acetic acid)trithiocarbonate (DATC) as the chain transfer agent. There are a wide variety of different possible end groups for zSMA should different RAFT chain transfer agents be chosen for the preparation of zSMA via RAFT polymerization, should the residue RAFT chain transfer moieties on zSMA be cleaved or converted to other groups, or should the zSMA be prepared via other polymerization methods, including but not limited to anionic polymerization, cationic polymerization, conventional free radical polymerization, or other types of controlled/living free radical polymerization such as atom transfer radical polymerization (ATRP), nitroxide mediated polymerization (NMP), etc.

The present invention overcomes the problems in the prior art with coordination of the SMA carboxyl acids with the immobilized $Ni^{2+}$ or $Co^{2+}$ used for His tag-based membrane protein purification, and SMA precipitation that follows electrostatic association of the carboxylates with $Ca^{2+}$, $Mg^{2+}$ and polyvalent cations in general[12,15]. As a result, assays that require lowering pH to 6 or less (e.g., determination of acidification-induced rhodopsins spectral shifts, activation of ion channels such as KcsA) or studies of ATPases that require $Mg^{2+}$ (e.g., ion pumps, ATP-binding cassette proteins) cannot be performed with the proteins in a functional state and reconstituted in SMALPs. Some of the incompatibilities of SMALPs are illustrated in FIG. 1A. The images show the solubilization of E. coli membranes containing proteorhodopsin (PR), which gives the pinkish color to the samples. For these studies, the inventors used Xiran S Z25010 (a gift from Polyscope Polymers (Geleen, The Netherlands). This compound, referred throughout as SMA, is a styrene-maleic acid copolymer with a molar ratio of styrene-to-maleic acid of 3:1 and an average molecular mass of 10 kDa[16-19]. The clear supernatant of the SMA-treated sample, after removal of insoluble material by centrifugation (tube 3 vs. tube 1), clearly illustrates the known solubilizing property of SMA copolymers[12-15]. However, addition of 5 mM $MgCl_2$ (tube 4) or $CaCl_2$ (tube 5) or reducing the pH from 7.5 to 5.0 (tube 6) results in precipitation of the SMALPs. Recently, a diisobutylene/maleic acid copolymer (DIBMA) was tested for solubilization and formation of nanoparticles equivalent to SMALPs[16]. This copolymer does not precipitate in the presence of divalent cations[16], but it can precipitate at acidic pH because it contains the same carboxyl acids as that in commercial SMA[20].

Figure 1B:
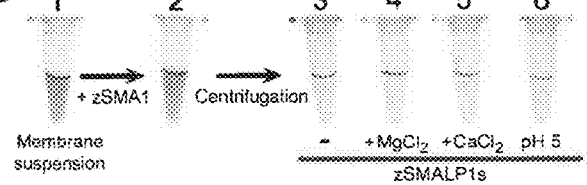
Figure 1C:
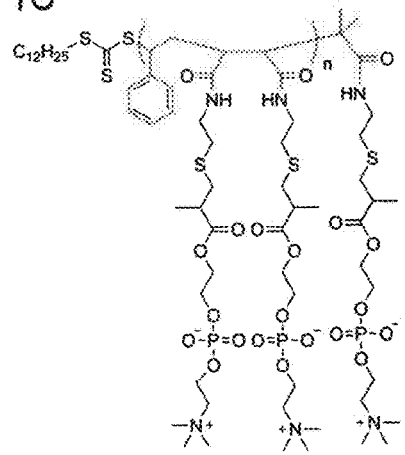

To overcome the buffer incompatibilities of SMALPs, the present inventors designed and synthesized a SMA-related copolymer where the anionic carboxyl acid groups were converted to zwitterionic phosphatidylcholine groups through stable amide bonding (FIG. 1C). The inventors synthesized three new copolymers where the number of repeats (n in FIG. 1C) was 59 (zSMA1), 106 (zSMA2)15 (zSMA3). Even though maleic acid is not part of the new copolymers, the inventors named them zSMAs (z for zwitterionic) because of the widespread use of the term SMALPs. In this study, the inventors present data on formation of zSMALPs by the three new copolymers, but focused on zSMA1, which produces zSMALPs similar in size to SMALPs formed by Xiran. Details on the synthesis and characterization of the zSMA polymers are presented in the Methods and FIGS. 3 to 6.

Figure 1D:
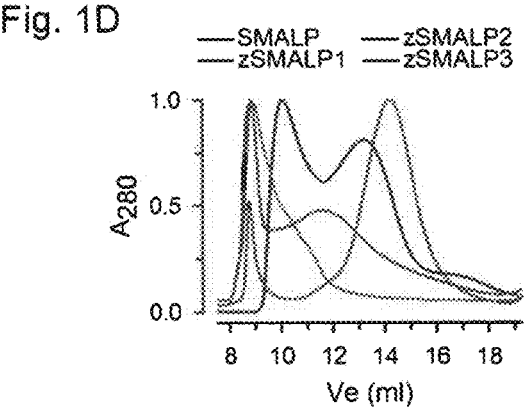
Figure 1E:
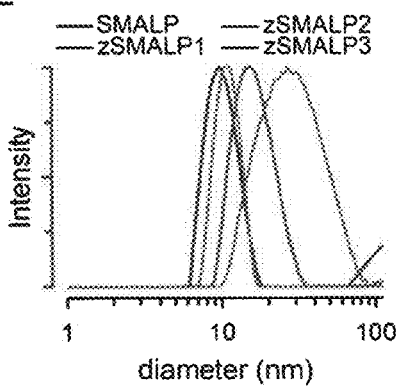
Figure 1F:
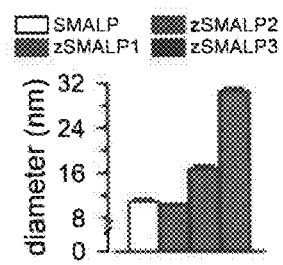

FIG. 1B shows that zSMA1 can also solubilize membranes, but as expected from its design without the carboxylate group (FIG. 1C) zSMALP1s remain in solution in the presence of divalent cations or after lowering the pH (FIG. 1B). For the particular case of PR expressed in E. coli, the solubilization of the protein was 62±4% (n=4) of the total protein present in the crude membranes. The size-exclusion chromatogram in FIG. 1D shows that the zSMALP1s formed by solubilization of liposomes are more uniform in size than SMALPs, and that zSMALP2s are larger; the zSMALP3s are even larger (not shown because their peak run too close to the aggregates at the lower elution volumes). The hydrodynamic diameter, determined by dynamic light scattering (DLS), for the peaks pointed by the arrows in FIG. 1D is shown in FIG. 1E. The values for SMALPs are consistent with previous estimations[12]. As expected from the data in FIG. 1D, the zSMALP1s size is similar, but more uniform, than that of SMALPs (FIG. 1E). The averages in FIG. 1F show that the diameters correlate with the size of the copolymer (zSMA3>zSMA2>zSMA1=SMA). The possibility of controlling the particle size could be exploited to engineer optimum zSMALPs for specific applications.

Figure 2A:
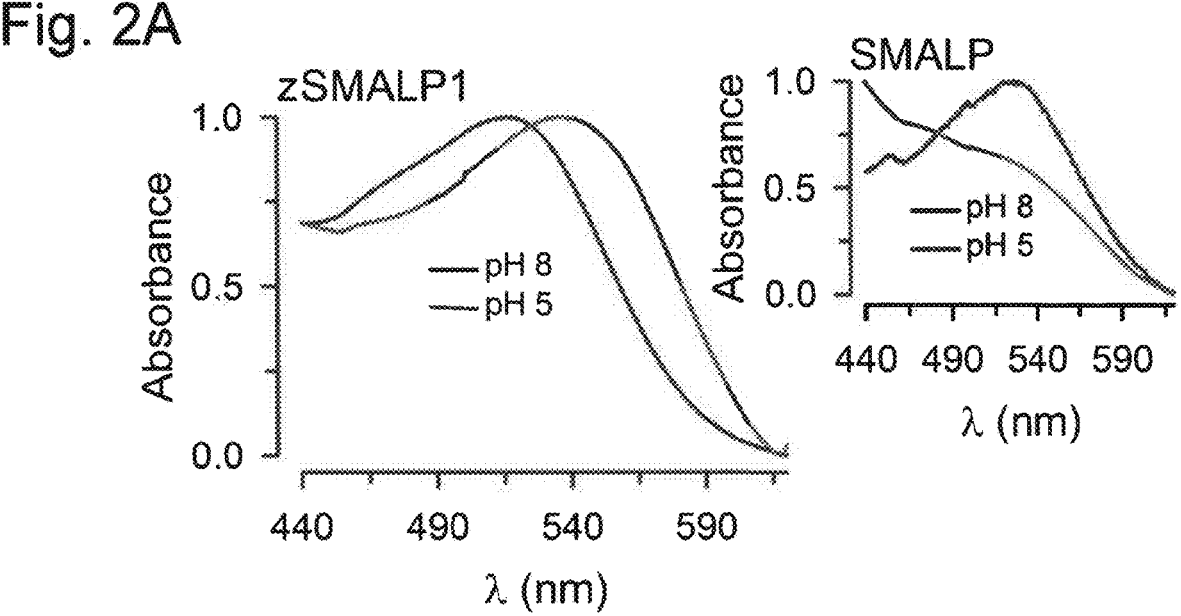
FIGS. 2A and 2B show functional assays of proteorhodopsin and MsbA in nanodiscs formed by zSMALP1.
Figure 2B:
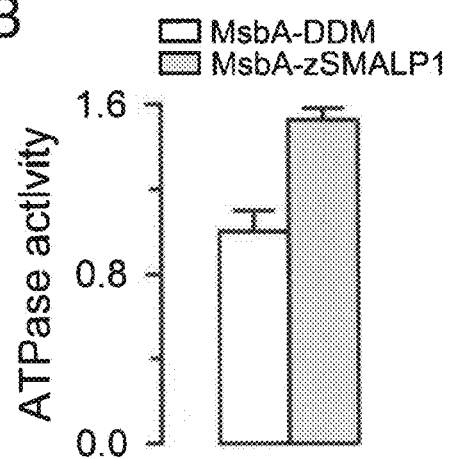
Figure 8:
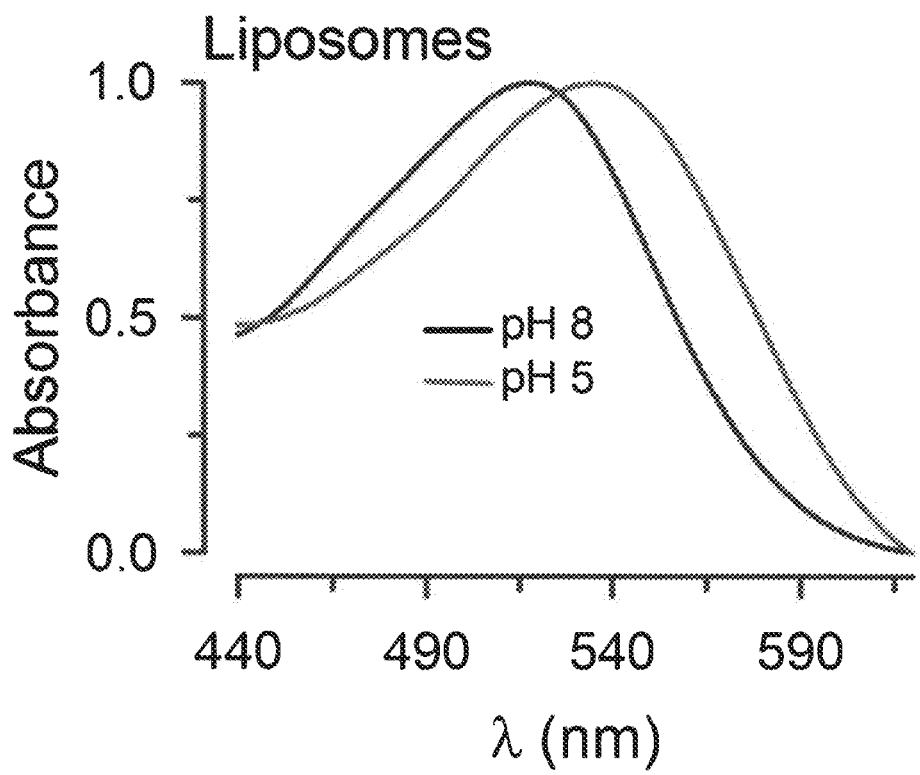
FIG. 8 shows a functional assay of proteorhodopsin reconstituted in liposomes. pH-induced PR spectral shift elicited by lowering from 8 to 5. The data were normalized to the peak absorbance.
Figure 9:
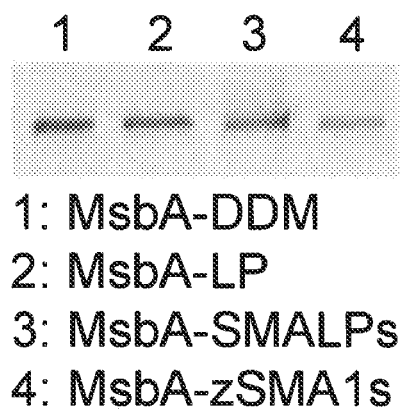
FIG. 9 shows the reconstitution of MsbA into SMALPs and zSMALP1s. Lane 1 (MsbA-DDM): purified MsbA in DDM; lane 2 (MsbA-LP): purified MsbA reconstituted into liposomes; lane 3 (MsbA-SMALP): MsbA reconstituted into liposomes and solubilized into SMALPs; lane 4 (MsbA-zSMALP1): MsbA reconstituted into liposomes and solubilized into zSMALP1s. The data correspond to immunoblots using a primary antibody against the His tag fused to the N-terminal end of MsbA.

Next, the inventors focused on testing the usefulness of zSMA1 for functional studies of membrane proteins that require divalent cations or lowering pH. The spectral shift elicited by lowering pH is a basic functional assay of rhodopsin-like proteins such as PR. For these studies, purified PR incorporated in liposomes was solubilized/reconstituted with SMA or zSMA1 (see Methods and FIG. 7A-7B). The typical spectral shift produced by lowering pH (see FIG. 8)[21] can be easily seen in the PR-loaded zSMALP1s, whereas such an assay cannot be performed in SMALPs because of the precipitation upon lowering pH (FIG. 1A and FIG. 2A inset). The shift wavelength maxima by lowering pH from 8 to 5 was similar for PR in zSMALP1s (19.8±0.2 nm; n=3) and PR in detergent or liposomes (18.0±0.8 nm; n=4). Similarly, purified MsbA (an ATP-binding cassette transport ATPase) reconstituted in liposomes can be solubilized into SMALPs and zSMALP1s (FIG. 9). However, the ATPase activity of this ABC protein can be evaluated only with the protein reconstituted into zSMALP1s (FIG. 2B) because the $Mg^{2+}$ required for its ATPase activity causes precipitation of SMALPs (FIG. 1A).

In summary, the present invention is a new zSMA1 copolymer, which does not have the carboxyl acids present in SMA, and can solubilize membrane proteins from membranes and liposomes. Different from SMALPs, the new zSMALPs are compatible with solutions of lower pH and the presence of millimolar multivalent cations. The present invention also shows that it is possible to control the size of the zSMALPs by modification of the copolymer size. The zSMALPs can expand the use of these polymer-encased bilayer nanostructures to studies of a large group of membrane proteins in a functional state, including P-type, F-type, V-type and ABC ATPases, as well as allow for studies of the regulation of membrane proteins by pH and divalent cations.

Figure 3:
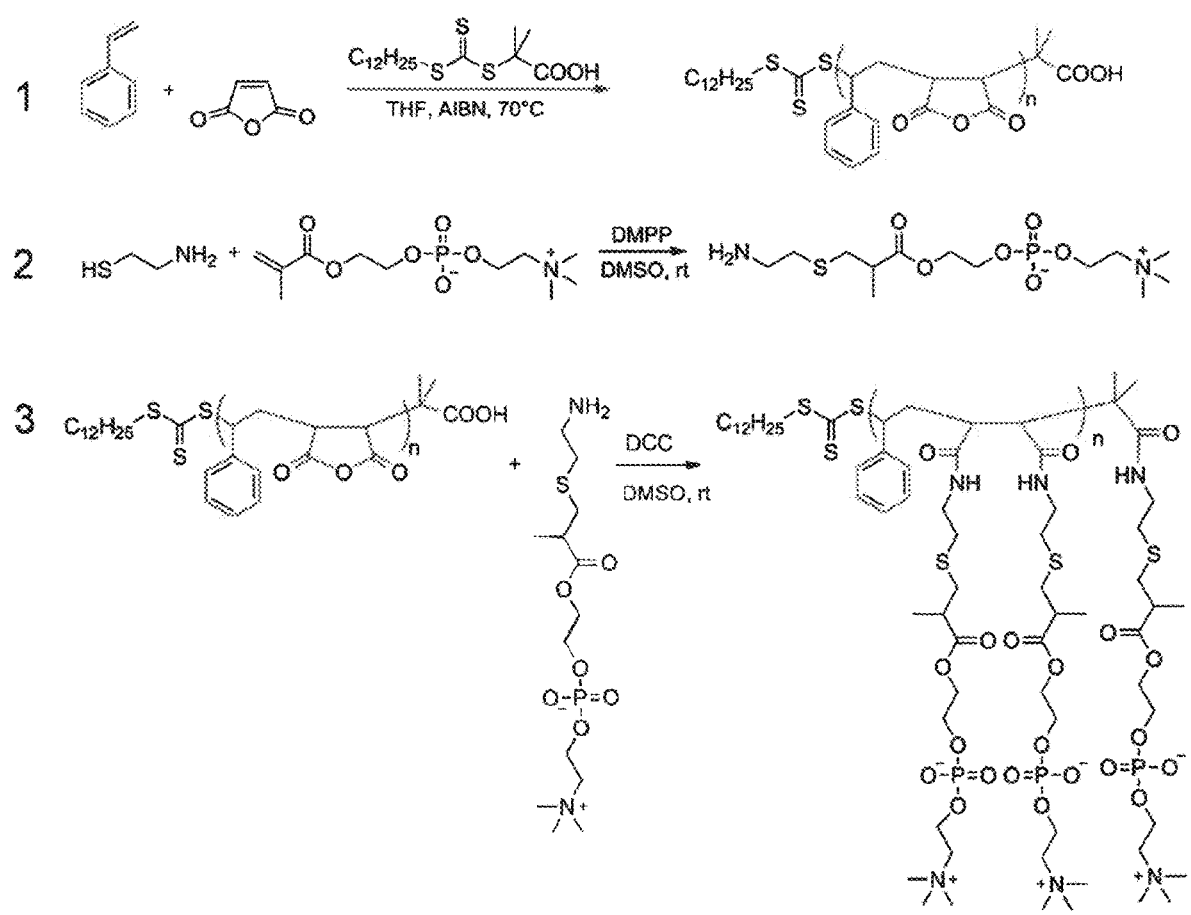
FIG. 3 shows the structure of cysteamine-PC modified alternating polymer P(S-at-MA)$_n$ as an example of zSMA See details below.

Polyvalent modified alternating polymer P(S-at-MA). All chemicals employed were of the highest quality/purity available, and were used as received, except for styrene (inhibited with 0.005% 4-tert-butylcatechol), azobisisobutyronitrile (AIBN) and S-1-dodecyl-S'-(α,α'-dimethyl-α"-acetic acid) trithiocarbonate (DATC). Styrene (Sigma-Aldrich, St. Louis, Mo.) was purified by passing through a basic aluminum oxide ($Al_2O_3$) column before use, and AIBN (Sigma-Aldrich) was re-crystallized from methanol twice before use. DATC was synthesized according to literature[22]. Alternating copolymers P(S-at-MA) of different size were synthesized by the reversible addition-fragmentation chain transfer (RAFT) polymerization method with DATC as the chain transfer agent and AIBN as the initiator (reaction schemes are presented in FIG. 3). In a typical reaction (FIG. 3, scheme 1A), styrene (2.08 g, 20 mmol), maleic anhydride (2.00 g, 20.4 mmol), DATC (18.3 mg, 0.05 mmol) and AIBN (1.6 mg, 0.01 mmol) were dissolved in 5.6 ml tetrahydrofuran (THF) in a 10-ml Schlenk flask, stirred, and degassed by three freeze-pump-thaw cycles. Then, the flask was sealed and immersed in a 70° C. oil bath, and after a predetermined time the reaction was quenched by liquid nitrogen. The mixture was then diluted with THF and precipitated three times with an excess of ether/chloroform. The reaction conditions and conversions are summarized in Table 1. To synthesize cysteamine modified phosphorylcholin, 2-methacryloyloxyethyl phosphorylcholin was reacted with cysteamine via the thiol-ene "click" reaction[23] (FIG. 3, scheme 1B). Briefly, cysteamine (0.74 g, 9.50 mmol), 2-methacryloyloxyethyl phosphorychroline (2.80 g, 9.48 mmol) and DMPP (66.3 mg, 0.48 mmol) were dissolved in 8 ml of dimethylsulfoxide (DMSO) in a 25-ml flask. After stirring for 2 days at room temperature the solution was precipitated twice with acetone/ether (2/1). The total amount of product (cysteamine-PC) was 3.3 g, with a yield of 93.2%. P(S-at-MA) was modified with the cysteamine-PC as shown in FIG. 3 (scheme 1C). In a typical run, P(S-at-MA) (0.12 g, 0.6 mmol maleic anhydride) dissolved in 10 ml of DMSO was added into a 50-ml flask containing cysteamine-PC (0.60 g, 1.61 mmol), dicyclohexylcarbodiimide (DCC) (0.31 g, 1.5 mmol) and 15 ml of DMSO. After stirring for 2 days at room temperature the solid formed was filtered away and the solution was dialyzed in water for two days. The solvent was evaporated after filtering away the insoluble material, and the product was re-dissolved with DMSO and then precipitated twice into acetone/ether (3/1). The product was collected by centrifugation, dried in vacuum and characterized by $^1H$ NMR.

TABLE 1

Sample Conditions for the RAFT polymerization of the P(S-at-MA) copolymers and conversion.

| Sample | [Monomer] | [S]/[MA]/[CTA]/[I] | Reaction time | Conversion |
|---|---|---|---|---|
| P(S-at-MA)$_{59}$ | 5M | 59/62/1/0.125 | 6 h | 99% |
| P(S-at-MA)$_{106}$ | 5M | 400/408/1/0.125 | 2 h | 26% |
| P(S-at-MA)$_{215}$ | 5M | 400/410/1/0.125 | 3.5 h | 53% |

S: styrene; MA: maleic anhydride; CTA: cysteamine; I: initiator, azobisisabutyronitrile (AIBN).

TABLE 2

Molecular weights and polydispersity indexes before PC modification.

| Sample | MW from conversion | MW from NMR | GPC in DMF | |
|---|---|---|---|---|
| | | | Mn | PDI |
| P(S-at-MA)$_{59}$ | 12,451 | 12,675 | NA | 1.085 |
| P(S-at-MA)$_{106}$ | 21,576 | 21,777 | 35,000 | 1.170 |
| P(S-at-MA)$_{215}$ | 43,708 | 43,795 | 53,800 | 1.197 |
| SMA (Xiran) | NA | NA | NA | 1.341 |

MW: molecular weight; GPC: gel permeation chromatography; DMF: dimetylformamide; Mn: number average molecular weight; PDI: polydispersity index; NA: not available.

Figure 4A:
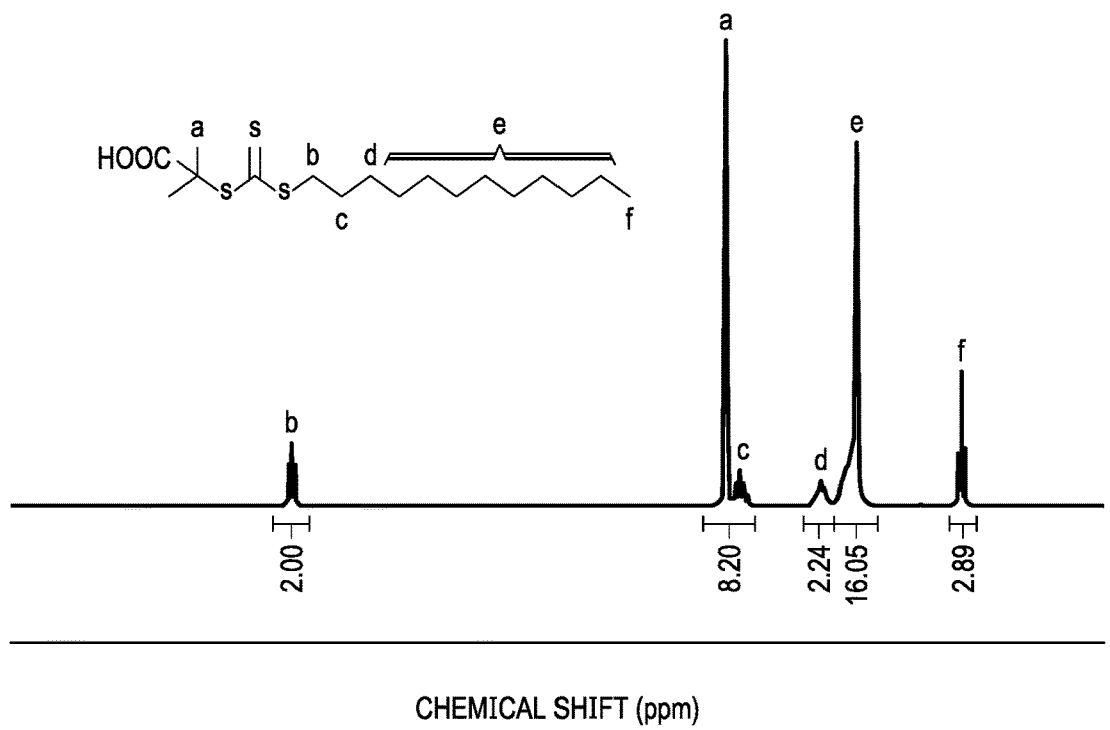
FIGS. 4A to 4D show NMR spectra of alternating copolymers.
Figure 4B:
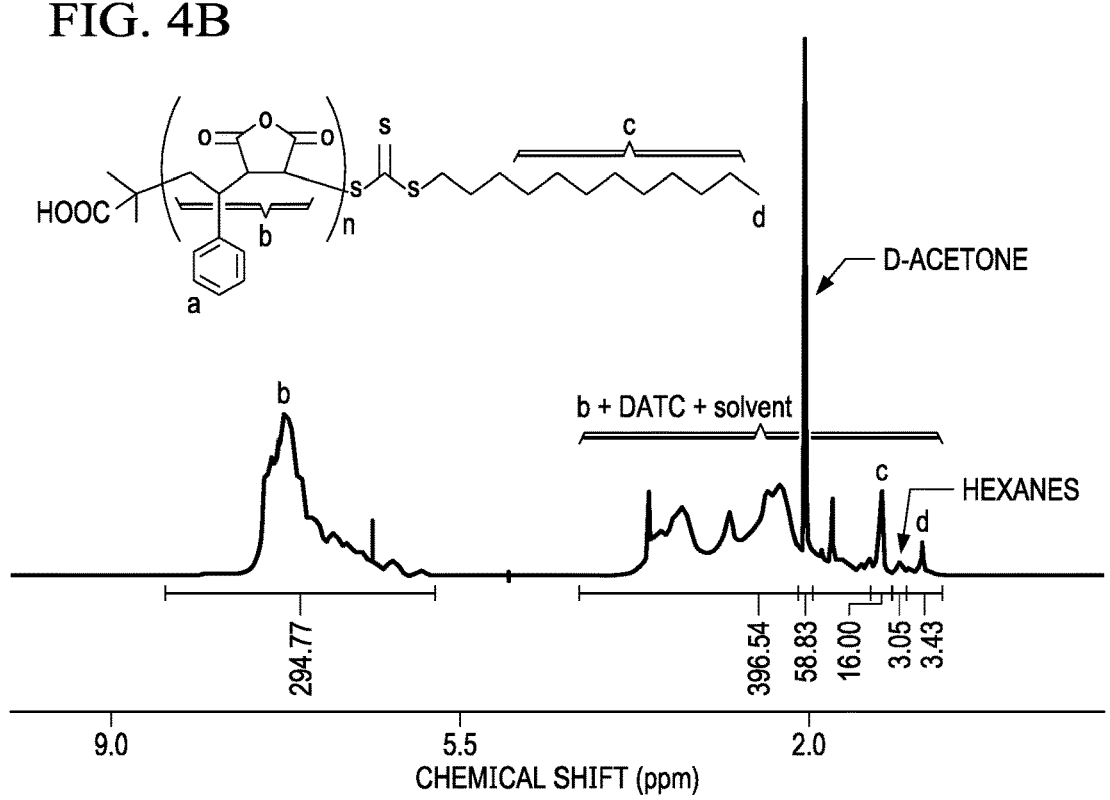
Figure 4C:
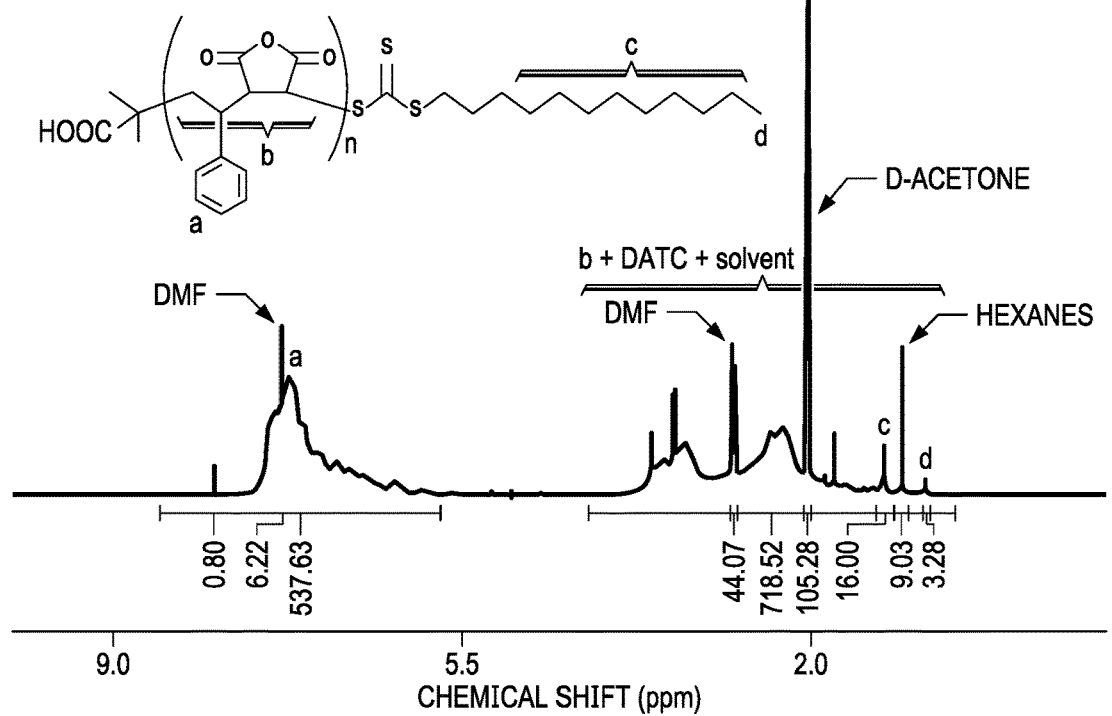
Figure 4D:
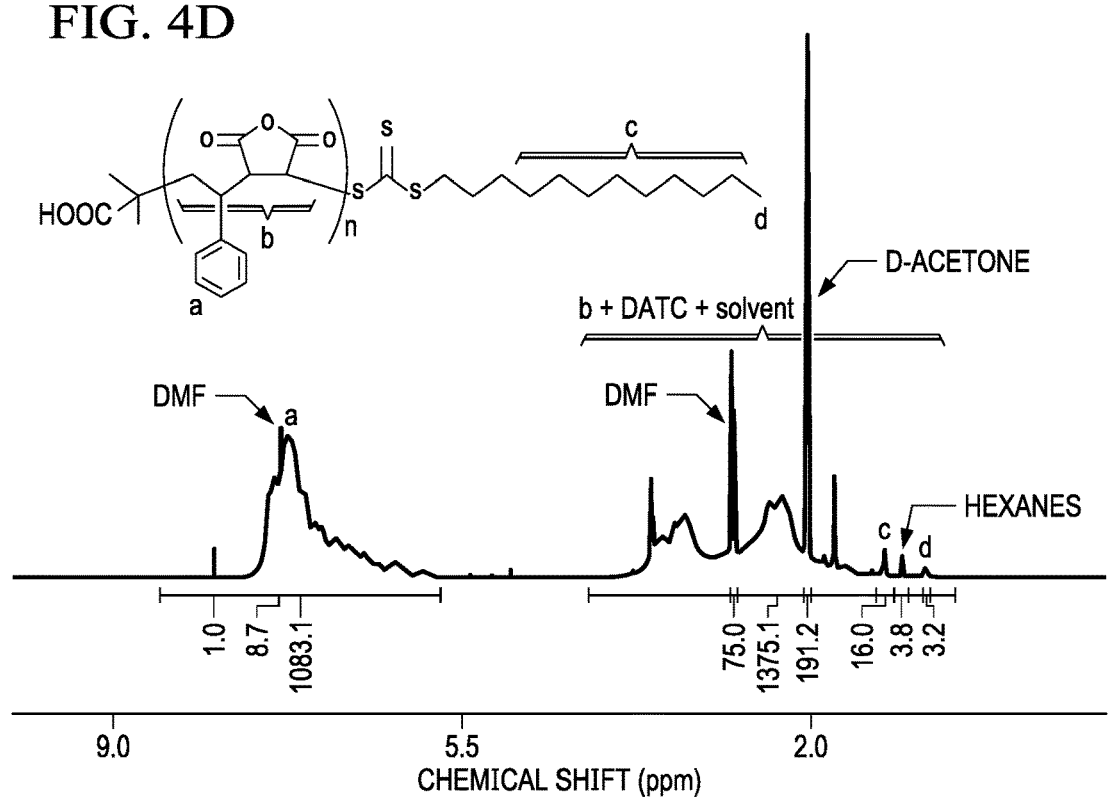

Characterization and Data Analysis. The chemical structures of the polymers were characterized by $^1H$ NMR (400 MHz liquid-state NMR spectrometer, Jeol, Peabody, Mass.), and the polymers size distribution was assessed by gel permeation chromatography (GPC) (Agilent 1260 HPLC system equipped with a Wyatt Optilab T-rEX refractive index detector and a Wyatt MiniDAWN TREOS multi-angle light scattering detector, using an Agilent PLgel 5 μm MIXED column (300×7.5 mm). For the GPC the system was equilibrated with dimethylformamide (DMF)/0.02 M ammonium acetate and run at 0.5 ml/min and 50° C.). The zeta potential was measured using a Zetasizer Nano ZSP (Malvern Instruments, Westborough, Mass.). The copolymerization of styrene and maleic anhydride is known to yield alternating polymers that contains a monomer ratio close to 1:1[24]. To characterize the size of the polymer and the ratio of styrene to maleic anhydride in the polymer we used NMR. The chain transfer agent DATC has 16 protons in its hydrocarbon tail at 1.17-1.32 ppm (FIG. 4A). This sharp peak was used as reference to characterize the structure of P(S-at-MA) because it is relatively undisturbed from other peaks. The NMR spectrum of P(S-at-MA)$_{59}$ is shown in FIG. 4B. When the peak at 1.17-1.32 ppm was set at 16 protons, there were 295 protons from the benzene ring of the styrene ($N_a$) located at 5.70-8.50 ppm. The chemical shift of protons from the backbone was mixed with those from solvents such as hexanes, acetone, dimethylformamide (DMF) and DATC. As a result, the number of protons (N) from the backbone ($N_b$) can be calculated only by subtracting the protons from solvents ($N_{solvents}$) and DATC ($N_{DATC}$) from the total number of protons ($N_{tot}$) of that range according to: $N_b = N_{tot} - N_{solvents} - N_{DATC}$. Assuming $N_{DATC}$ of 31 and $N_{solvents}$ from acetone-$d_6$ and hexanes of 58.83 and 3.05, respectively, $N_b = 303.63$.

Each styrene and maleic anhydride contributes 3 and 2 protons to the backbone, respectively. The average degree of polymerization (DP) of styrene can be calculated as $DP_S = N_a/5 = 59$, so the average DP of maleic anhydride ($DP_{MA}$) is: $DP_{MA} = (N_b - DP_S \times 3)/2$. The $DP_{MA}$ calculated was 63, and $DP_{MA}/DP_S$ was 1.07, a value very close to 1/1, and also to the ratio calculated from conversion. The same method was used to calculate the DP and monomer ratio of the other two P(S-at-MA) polymers, which were identified as P(S-at-MA)$_{106}$ (FIG. 4C) with $DP_S = 106$ and $DP_{MA}/DP_S = 1.00$, and P(S-at-MA)$_{215}$ (FIG. 4D) with $DP_S = 215$ and $DP_{MA}/DP_S = 1.00$).

Figure 5A:
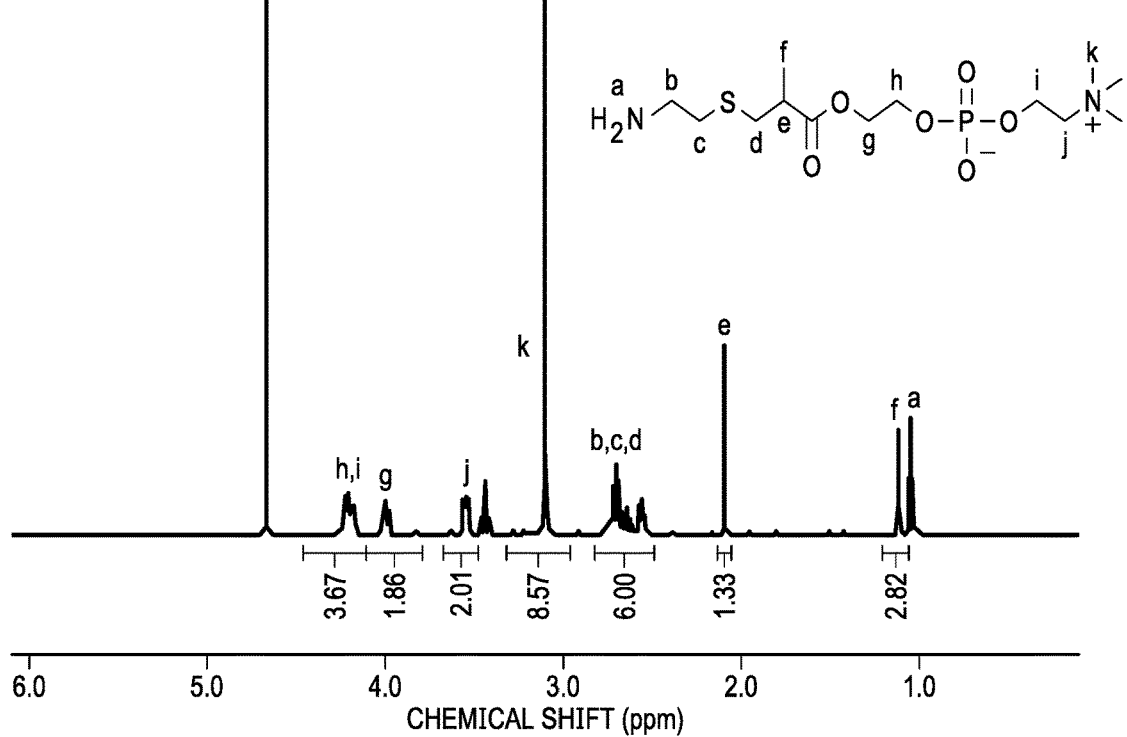
FIGS. 5A to 5D show NMR spectra of cysteamine-PC-modified alternating copolymers.

Cysteamine-PC was also characterized by NMR (FIG. 5A). The chemical shifts of 6 protons b, c and d shown on the structure of cysteamine-PC (FIG. 5A inset) is in the 2.50-2.80 ppm range, and was used as reference. There were ~4 protons at 4.10-4.45 ppm (h, i), ~2 protons at 3.80-4.10 ppm (g), 2 protons at 3.48-3.67 ppm (j), ~9 protons at 2.97-3.30 ppm (k) and ~1 proton at 2.06-2.13 ppm (e). The number and position of those protons is in agreement with the structure of PC, suggesting that the cysteamine modified PC was synthesized successfully.

Figure 5B:
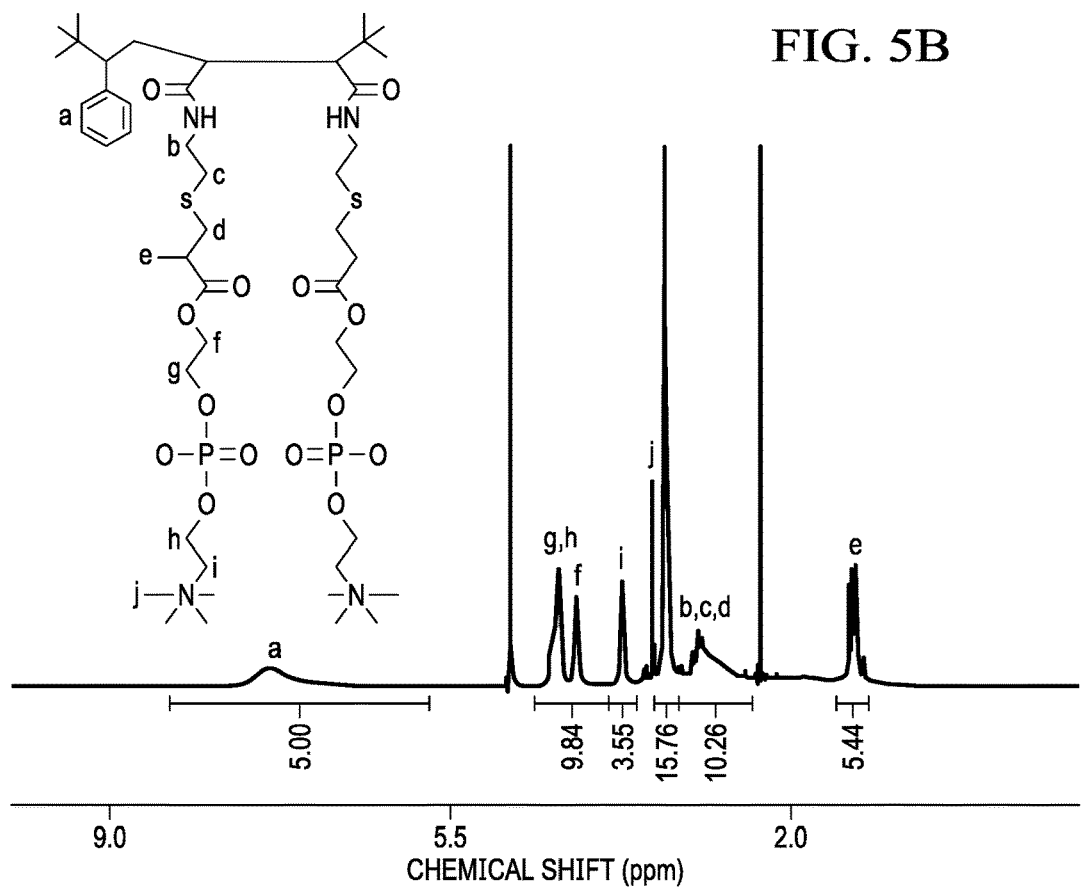
Figure 5C:
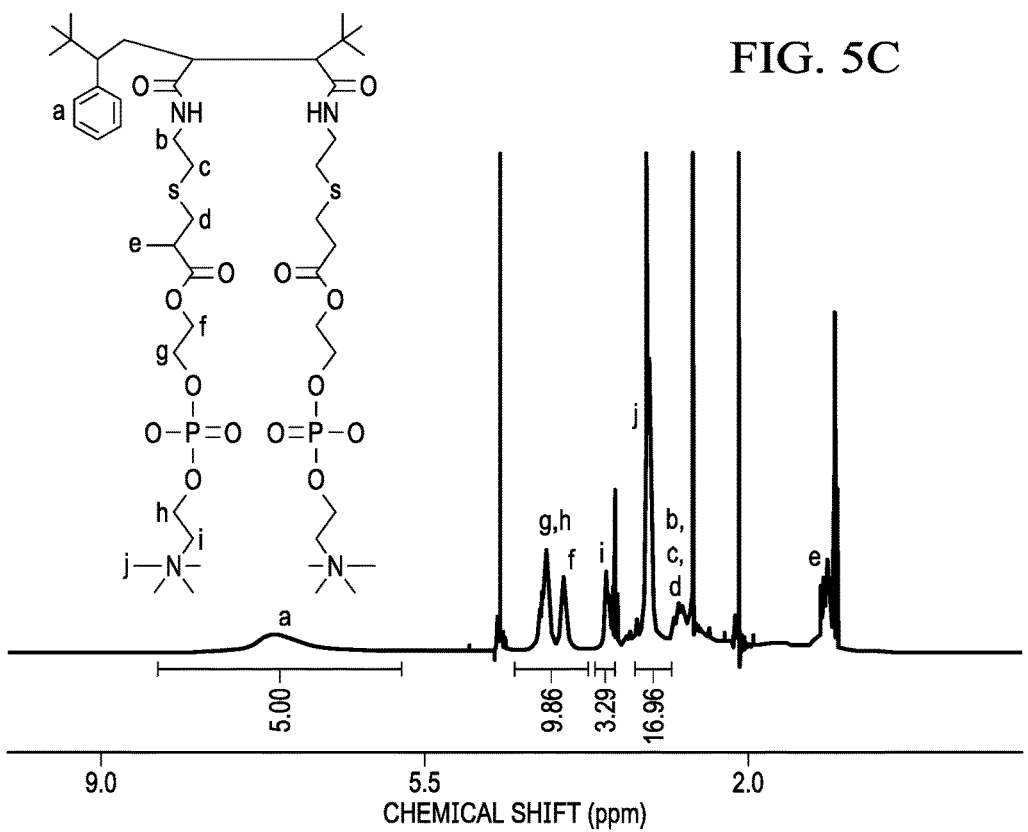
Figure 5D:
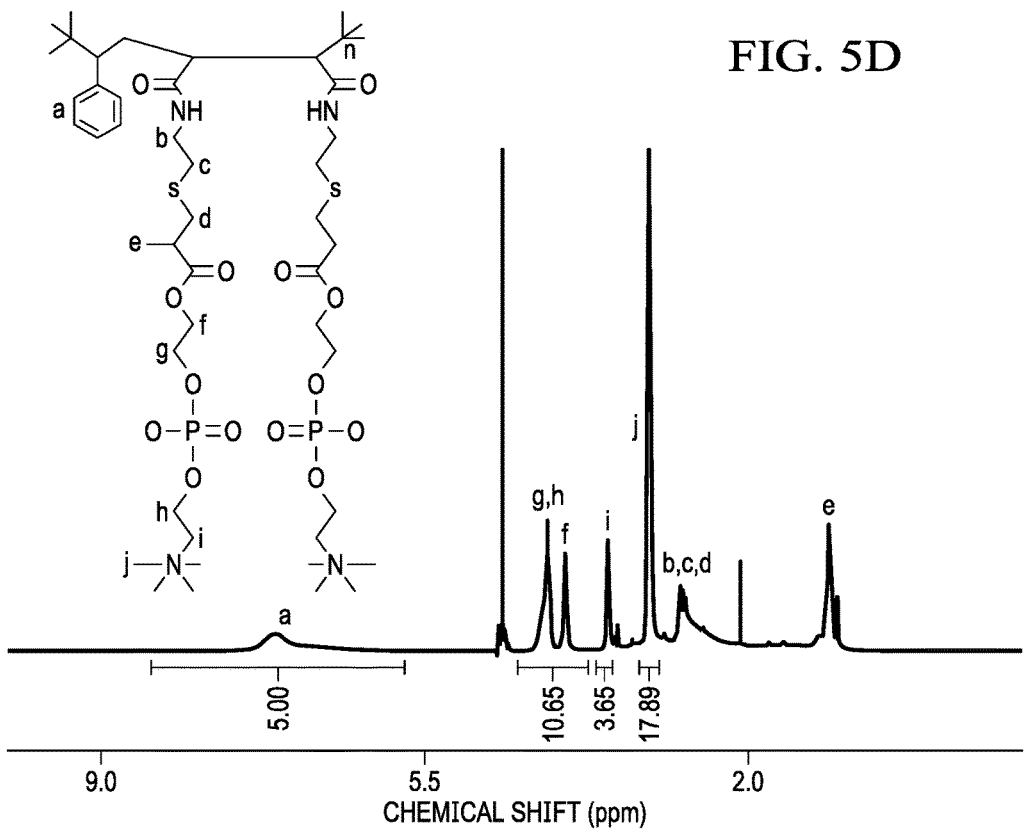

NMR was also used to characterize the alternating polymer structure after modification with cysteamine-PC. The styrene structure was not affected by the modification and it was used as reference to calculate the portion of modified maleic anhydride moiety. The NMR spectrum of cysteamine-PC-modified P(S-at-MA)$_{59}$ is shown in FIG. 5B. The number of protons from the benzene located at 5.70-8.50 ppm (peak a) was set to 5. Since the ratio of maleic anhydride/styrene is nearly 1, when maleic anhydride was fully reacted with cysteamine-PC a total of 12 protons for peak g, h and f is expected. The reason to use these proton peaks to calculate the percentage of modification is that they are mostly free from overlapping peaks of other protons. From the NMR spectrum $N_{g,h,f} = 9.84$ protons, and the percentage of modified maleic anhydride calculated as: $\omega = N_{g,h,f}/12 \times 100$ was therefore 82.0%. The percentage modification calculated for cysteamine-PC-modified P(S-at-MA)$_{106}$ (zSMA2; FIG. 5C) and cysteamine-PC-modified P(S-at-MA)$_{215}$ (zSMA3; FIG. 5D) were 82.2 and 88.8%, respectively.

For determinations of the zeta potential commercial SMA and P(S-at-MA)$_{215}$ were dissolved to ~1 mg/ml in 50 mM Tris/HCl, pH 8.0, 100 mM NaCl, and the solutions were filtered through a 0.2-μm syringe filter before analysis. As expected, commercial SMA exhibited a negative average surface zeta potential; its value of −36.7 mV (FIG. 6, black) contrasted with that of nSMA1, which was nearly neutral at −2.8 mV (FIG. 6, red).

Expression and purification of proteorhodopsin. A synthetic gene (Genscript) coding for proteorhodopsin (PR) with a 6-His tag fused to the C-terminal end was cloned into the NcoI/BamHI sites of the expression vector pET19b. PR was overexpressed in the E. coli strain BL21 (DE3) codon plus (Agilent Technologies, Santa Clara, Calif.) transformed with the pET19-PR plasmid. The cells were grown in 2YT medium with 0.5% glucose, 200 μg/ml carbenicillin, 34 μg/ml chloramphenicol and 10 μM all-trans retinal, at 37° C. The cells were induced at OD$_{600}$~1 with 1 mM isopropyl-β-D-thiogalactopyranoside (IPTG). At induction, the inventors also added 10 μM of all-trans retinal, and the cells were harvested 4 h later. All subsequent procedures were performed at 4° C. unless specified otherwise. Cell pellets were resuspended in a buffer containing 50 mM potassium phosphate and 5 mM MgCl$_2$, pH 7.2, with 10 μg/ml lysozyme, 10 μg/ml DNAse I, 1 mM phenylmethanesulfonyl fluoride (PMSF) and a protease inhibitor cocktail (1 tablet/100 ml of buffer; complete EDTA-free, Roche, Manheim, Germany), and lysed on a microfluidizer. Crude membranes were prepared by centrifugation at 135,000 g for 1.5 h, and were solubilized overnight, at 4° C., in a buffer containing 150 mM KCl, 50 mM potassium phosphate, pH 8, 1 mM PMSF and 1.5% n-dodecyl-β-D-maltopyranoside (DDM; Inalco Pharmaceuticals), at a total protein concentration <2 mg/ml The DDM-solubilized lysate was obtained centrifuged at 100,000 g for 30 min, and the supernatant was incubated with Talon Co$^{2+}$ beads (Talon Superflow, Clontech) for 3 h. The resin was washed with 10 column volumes of buffer containing 150 mM KCl, 50 mM potassium phosphate, pH 8, 0.05% DDM and 40 mM imidazole. Imidazole was added to a concentration of 250 mM for elution. After elution, the imidazole was removed by exchanging the buffer to 10 mM Tris/HCl, pH 8.2, with 0.05% DDM. The purity of the preparation was assessed by staining gels (SDS PAGE) with Coomassie blue and UV-Vis spectroscopy. The PR samples were concentrated to 10 mg/ml, and stored at 4° C. until use.

Extraction of proteorhodopsin from crude membranes with SMA and zSMA1. For our comparative experiments we used the SMA copolymer Xiran SZ25010 from Polyscope Polymers (Geleen, The Netherlands). As mentioned in the main text, the inventors refer to this copolymer as SMA. SZ25010 was provided by Polyscope Polymers as a gift, in a sodium salt aqueous solution (Xiran SZ25010 S25). Crude membranes from E. coli cells expressing PR were prepared as described above. The membranes were resuspended at a final concentration of 40 mg/ml (wet membrane mass) in 150 mM NaCl, 50 mM Tris/HCl, pH 8, and 10% glycerol. SMA or zSMA1 were added to a final concentration of 2.5% (w/v) and the samples were incubated at room temperature with gentle rotation for 2 h. Non-soluble material was removed by centrifugation at 100,000 g for 30 min, at 4° C., and the supernatant containing PR-loaded SMALPs or zSMALP1s was analyzed for buffer compatibilities by addition of MgCl$_2$ or CaCl$_2$ to a final concentration of 5 mM, or by lowering the pH from 8 to 5 with HCl. The presence of PR in the crude membranes and copolymer-solubilized samples was determined by Western blotting using an antibody against the 6×His tag (anti-Hexa-His antibody, GenScript) fused to the C-terminal end of PR. The secondary antibody was a goat-anti-mouse Alexa Fluor 680 (Life Technologies), and the signal was visualized using an Odyssey Infrared Imager (Li-Cor Biosciences). The efficiency of PR solubilization in zSMALPs was quantified from the Western blots using densitometry (UN-SCAN-IT, Silk Scientific).

Solubilization/reconstitution of proteorhodopsin in SMALPs or zSMALPs. Stocks of 1,2-dioleoyl-sn-glycero-3-phosphocholine (DOPC), 1,2-dioleoyl-sn-glycero-3-phospho-(1'-rac-glycerol) (DOPG) in chloroform (Avanti Polar Lipids) were dried under a stream of argon followed by vacuum drying overnight. The dried lipids resuspended at a concentration of 10 mg/ml in 50 mM Tris/HCl, pH 8, with 4 mM DDM, were sonicated until clear. Proteoliposomes were obtained by reconstituting DDM-solubilized PR at 2:1 protein:lipid ratio (w/w) by gel filtration (Zeba columns, Thermo Fisher Scientific) pre-equilibrated with a solution containing 100 mM NaCl and 50 mM Tris/HCl, pH 8[25,26]. The lipids consisted of a 9:1 ratio (w/w) of DOPC:DOPG. After reconstitution, the samples were extruded through a 200-nm polycarbonate filter (Mini-Extruder, Avanti Polar Lipids). PR-liposomes were incubated with SMA or zSMA1 at a final concentration of 2.5% (w/v) for 2 h at room temperature. After incubation, non-solubilized material was removed by ultracentrifugation at 100,000 g for 30 min. The purity of the preparation was assessed in Coomassie blue-stained gels and by UV-Vis spectroscopy.

Proteorhodopsin functional assay. The function of PR was determined by the shift in absorption spectra elicited by lowering pH from 8 to 5. The absorption spectra of PR-loaded SMALPs or zSMALP1s PR in DDM or liposomes were collected on a Jasco spectrophotometer (model V-630) at 22° C. The spectra were recorded first at pH 8, and then after acidification to pH~5 by addition of 1 N HCl.

Preparation of liposomes. *E. coli* total lipids dissolved in chloroform (Avanti Polar Lipids) dried as described above were resuspended to a final concentration of 20 mg/ml in 100 mM NaCl, 20 mM Tris/HCl, pH 7.4, with 4 mM DDM, and sonicated until clear. Liposomes produced by gel filtration using Zeba spin columns pre-equilibrated with 100 mM NaCl and 20 mM Tris/HCl, pH 7.4, were extruded as described above. For solubilization and formation of SMALPs and zSMALPs the liposomes were incubated for 2 h at room temperature with SMA, zSMA1, zSMA2 or zSMA3 at a final concentration of 2.5% (w/v). The samples were centrifuged at 125,000 g for 30 min and the supernatants (200 µl) were analyzed by high-resolution size-exclusion chromatography using a Superdex 200 Increase 10/300 GL column (GE Healthcare) equilibrated with the same buffer. The flow rate was set at 0.5 ml/min and fractions of 1 ml were collected for isolation of relevant peaks used for further studies.

Estimation of SMALPs and zSMALPs size by dynamic light scattering. Dynamic Light Scattering (DLS) experiments were performed at 22° C. on a Zetasizer Nano ZSP (Malvern Instruments), using 40-µl disposable microcuvettes. For each determination, measurement were repeated at least 3 times, with each being a 15-scan average (each ~15-s long). Size-intensity and size-volume distributions were generated using the Zetasizer software version 7.11, and were analyzed using the protein analysis distribution.

Solubilization/reconstitution and function of MsbA in SMALPs and zSMALP1s. MsbA was expressed, purified and reconstituted in liposomes as described[6,27]. For reconstitution purified MsbA in DDM was mixed at 1:10 protein:lipid ratio (w/w) with *E. coli* total lipids (Avanti Polar Lipids) in 100 mM NaCl, 20 mM Tris/HCl, pH 7.4, with 0.1 mM TCEP. The liposomes containing MsbA were extruded through a 200-nm polycarbonate filter and incubated with SMA or zSMA1 at a final concentration of 2.5% (w/v) for 2 h at room temperature. After incubation, non-solubilized material was removed by centrifugation at 100,000 g for 30 min. The MsbA-loaded nanodiscs were enriched based on the affinity of the His-tagged MsbA for $Ni^{2+}$. The supernatant was mixed with Ni-NTA beads (Thermo Fisher Scientific) at a ratio of 100 µl of resin/ml of solubilized protein, and incubated at 4° C. overnight with gentle rotation. Then, the samples were transferred to a gravity flow column and the resin was washed with 10 column volumes of 100 mM NaCl, 20 mM Tris/HCl, pH 7.4, with 0.1 mM TCEP and 20 mM imidazole, and elution was achieved by increasing the concentration of imidazole to 200 mM. Eluted fractions were analyzed on gels (16% SDS-PAGE) stained with Instant Blue (Expedeon). The ATPase activity of MsbA was measured using a variant of the ATPase linked assay[27,28].

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB.

Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Wallin, E. & von Heijne, G. Genome-wide analysis of integral membrane proteins from eubacterial, archaean, and eukaryotic organisms. Protein science: a publication of the Protein Society 7, 1029-1038 (1998).
2. Stahlberg, H. et al. Two-dimensional crystals: a powerful approach to assess structure, function and dynamics of membrane proteins. FEBS letters 504, 166-172 (2001).
3. Patist, A., Kanicky, J. R., Shukla, P. K. & Shah, D. O. Importance of micellar kinetics in relation to technological processes. J Colloid Interface Sci 245, 1-15 (2002).
4. Rues, R. B., Dotsch, V. & Bernhard, F. Co-translational formation and pharmacological characterization of beta1-adrenergic receptor/nanodisc complexes with different lipid environments. Biochimica et biophysica acta 1858, 1306-1316 (2016).
5. Etzkorn, M. et al. Cell-free expressed bacteriorhodopsin in different soluble membrane mimetics: biophysical properties and NMR accessibility. Structure 21, 394-401 (2013).
6. Zoghbi, M. E., Cooper, R. S. & Altenberg, G. A. The Lipid Bilayer Modulates the Structure and Function of an ATP-binding Cassette Exporter. The Journal of biological chemistry 291, 4453-4461 (2016).
7. Leitz, A. J., Bayburt, T. H., Barnakov, A. N., Springer, B. A. & Sligar, S. G. Functional reconstitution of Beta2-adrenergic receptors utilizing self-assembling Nanodisc technology. Biotechniques 40, 601-602, 604, 606, passim (2006).
8. Hagn, F., Etzkorn, M., Raschle, T. & Wagner, G. Optimized phospholipid bilayer nanodiscs facilitate high-resolution structure determination of membrane proteins. Journal of the American Chemical Society 135, 1919-1925 (2013).
9. Brewer, K. D., Li, W., Horne, B. E. & Rizo, J. Reluctance to membrane binding enables accessibility of the synaptobrevin SNARE motif for SNARE complex formation. Proceedings of the National Academy of Sciences of the United States of America 108, 12723-12728 (2011).
10. Viegas, A., Viennet, T. & Etzkorn, M. The power, pitfalls and potential of the nanodisc system for NMR-based studies. Biol Chem (2016).
11. Denisov, I. G. & Sligar, S. G. Nanodiscs for structural and functional studies of membrane proteins. Nature structural & molecular biology 23, 481-486 (2016).
12. Dorr, J. M. et al. The styrene-maleic acid copolymer: a versatile tool in membrane research. Eur Biophys J 45, 3-21 (2016).
13. Knowles, T. J. et al. Membrane proteins solubilized intact in lipid containing nanoparticles bounded by styrene maleic acid copolymer. Journal of the American Chemical Society 131, 7484-7485 (2009).
14. Jamshad, M. et al. Surfactant-free purification of membrane proteins with intact native membrane environment. Biochemical Society transactions 39, 813-818 (2011).
15. Rothnie, A. J. Detergent-Free Membrane Protein Purification. Methods in molecular biology 1432, 261-267 (2016).
16. Oluwole, A. O. et al. Solubilization of Membrane Proteins into Functional Lipid-Bilayer Nanodiscs Using a Diisobutylene/Maleic Acid Copolymer. Angewandte Chemie 56, 1919-1924 (2017).
17. Morrison, K. A. et al. Membrane protein extraction and purification using styrene-maleic acid (SMA) copolymer: effect of variations in polymer structure. The Biochemical journal 473, 4349-4360 (2016).
18. Dominguez Pardo, J. J. et al. Solubilization of lipids and lipid phases by the styrene-maleic acid copolymer. Eur Biophys J 46, 91-101 (2017).
19. Scheidelaar, S. et al. Effect of Polymer Composition and pH on Membrane Solubilization by Styrene-Maleic Acid Copolymers. Biophysical journal 111, 1974-1986 (2016).
20. BASF. Sokalan C P 9. Document TI/ES 1056 e. (2000).
21. Friedrich, T. et al. Proteorhodopsin is a light-driven proton pump with variable vectoriality. Journal of molecular biology 321, 821-838 (2002).
22. Lai, J. T., Filla, D. & Shea, R. Functional polymers from novel carboxyl-terminated trithiocarbonates as highly efficient RAFT agents. Macromolecules 35, 6754-6756 (2002).
23. Li, G. Z. et al. Investigation into thiol-(meth)acrylate Michael addition reactions using amine and phosphine catalysts. Polym Chem-Uk 1, 1196-1204 (2010).
24. Baruah, S. D. & Laskar, N.C. Styrene-maleic anhydride copolymers: Synthesis, characterization, and thermal properties. J Appl Polym Sci 60, 649-656 (1996).
25. Fiori, M. C. et al. Permeation of calcium through purified connexin 26 hemichannels. The Journal of biological chemistry 287, 40826-40834 (2012).
26. Kuang, L. et al. "Frozen" block copolymer nanomembranes with light-driven proton pumping performance. ACS Nano 8, 537-545 (2014).
27. Cooper, R. S. & Altenberg, G. A. Association/dissociation of the nucleotide-binding domains of the ATP-binding cassette protein MsbA measured during continuous hydrolysis. The Journal of biological chemistry 288, 20785-20796 (2013).

28. Urbatsch, I. L., Sankaran, B., Weber, J. & Senior, A. E. P-glycoprotein is stably inhibited by vanadate-induced trapping of nucleotide at a single catalytic site. The Journal of biological chemistry 270, 19383-19390 (1995).

What is claimed is:

1. A method of making a nanodisc with improved buffer compatibility comprising:
    mixing the one or more integral membrane proteins in a lipid layer with a polymer comprising a styrene-maleic acid derivative repeating units that carries zero or nearly zero net negative charge:

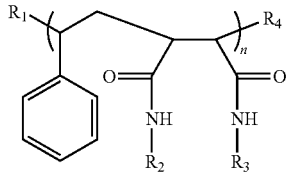

wherein the distribution of styrene and maleic acid derivative repeating units is random, wherein the nanodiscs are compatible with at least one of polyvalent cations, $MgCl_2$, $CaCl_2$, or pH<5, wherein $R_1$, $R_2$, $R_3$, and $R_4$ are selected from hydrogen; deuterium; a halogen group; a nitrile group; a nitro group; an imide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group including one or more of N, O, or S atoms; and wherein n is 1 to 200.

2. The method of claim 1, wherein $R_1$, $R_2$, $R_3$, and $R_4$, respectively, and the styrene and maleic acid are derivative units.

3. The method of claim 1, wherein at least one of $R_2$ or $R_3$ are bonded with the polymer repeating units via ester bond(s), ether bond(s), thioester bond(s), alkyl bond(s) or other chemical bonds; or wherein at least one of $R_1$ or $R_4$ can be also bonded with the polymer backbone via other forms of chemical bonding selected from an amide, ester, ether, silyl, or urea.

4. The method of claim 1, wherein the maleic acid derivative unit is converted from maleic anhydride unit in a styrene-maleic anhydride copolymer ratio of 4:1 to 1:4.

5. The method of claim 1, further comprising the step of forming a styrene repeating unit and a maleic acid derivative repeating unit; selecting a ratio of styrene repeating units to maleic acid derivative repeating is varied during synthesis; selecting a ratio of styrene repeating units to maleic acid derivative repeating is controlled during synthesis to control an average polymer molecular weight; forming the polymer into a nanodisc having a diameter that is tuned by controlling a size of the styrene-maleic acid derivative copolymers; or varying a copolymer of styrene to maleic anhydride ratio during synthesis based on a monomer feeding ratio resulting in copolymers that differ from a 1:1 alternation.

6. The method of claim 1, wherein the one or more integral membrane proteins are at least one of: soluble at a pH<7.0, soluble in the presence of cations, are adapted for the determination of acidification-induced rhodopsins spectral shifts, activation of ion channels such as KcsA), or measurement of ATPases; are rhodopsins, ion pumps, ATP-binding cassette proteins; or are at least one of P-type, F-type, V-type, or ABC ATPases.

7. The method of claim 1, wherein the lipids comprise lipids isolated from cells, or are synthetic lipids.

8. The method of claim 1, wherein n is 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 185, 190, 195, or 200.

9. The method of claim 1, wherein one or more end groups of zSMA are introduced by reversible addition-fragmentation chain-transfer (RAFT) polymerization in the preparation of zSMA using S-1-dodecyl-S'-($\alpha,\alpha'$-dimethyl-$\alpha''$-acetic acid)trithiocarbonate (DATC) as the chain transfer agent, wherein the end group are optionally $C_{12}H_{25}$—S—(C=S)—S—, or the one or more end groups of zSMA introduced by RAFT chain transfer agents that are cleaved or converted to other groups.

10. The method of claim 1, wherein the zSMA is prepared via other polymerization methods selected from at least one of anionic polymerization, cationic polymerization, conventional free radical polymerization, or other types of controlled/living free radical polymerization such as atom transfer radical polymerization (ATRP), and nitroxide mediated polymerization (NMP).

* * * * *